United States Patent
Liu et al.

(10) Patent No.: US 10,519,132 B2
(45) Date of Patent: Dec. 31, 2019

(54) ISOCORYDINE DERIVATIVES, PREPARATION METHOD AND USE THEREOF

(71) Applicant: Lanzhou Institute of Chemical Physics, Chinese Academy of Sciences, Lanzhou, Gansu (CN)

(72) Inventors: Junxi Liu, Gansu (CN); Duolong Di, Gansu (CN)

(73) Assignee: Lanzhou Institute of Chemical Physics, Chinese Academy of Sciences, Lanzhou (CN)

( * ) Notice: Subject to any disclaimer, the term of this patent is extended or adjusted under 35 U.S.C. 154(b) by 0 days.

(21) Appl. No.: 15/981,979

(22) Filed: May 17, 2018

(65) Prior Publication Data

US 2018/0334448 A1 Nov. 22, 2018

(30) Foreign Application Priority Data

May 18, 2017 (CN) .......................... 2017 1 0350678

(51) Int. Cl.

| C07D 401/12 | (2006.01) |
|---|---|
| A61K 31/40 | (2006.01) |
| C07D 211/18 | (2006.01) |
| A61P 35/00 | (2006.01) |

(52) U.S. Cl.
CPC ............ *C07D 401/12* (2013.01); *A61K 31/40* (2013.01); *A61P 35/00* (2018.01); *C07D 211/18* (2013.01); *Y02P 20/582* (2015.11)

(58) Field of Classification Search
CPC .................................................. C07D 401/12
See application file for complete search history.

(56) References Cited

FOREIGN PATENT DOCUMENTS

| CN | 103664782 A | 3/2014 |
| CN | 104072418 A | 10/2014 |
| CN | 105315208 A | 2/2016 |
| CN | 107488146 A | 12/2017 |

OTHER PUBLICATIONS

Pinedo et al. (2000).*
McMahon et al. (2000).*
Neidle et al. (2008).*

(Continued)

Primary Examiner — Paul V Ward

(74) *Attorney, Agent, or Firm* — Enshan Hong; VLP Law Group LLP

(57) ABSTRACT

A derivative of isocorydine of formula I:

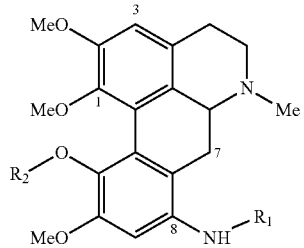

Formula I wherein:
$R_1 =$

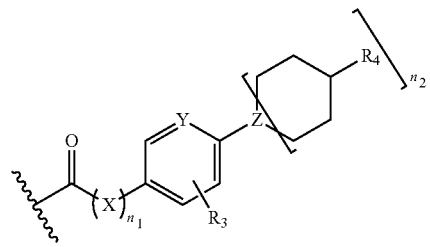

$X = N, C, C = C; n_1 = 0, 1$
$R_2 = H, R_1\ Y = C, N$
$R_3 = H, Cl, Br, F, CF_3, OCH_3, CH_3,$

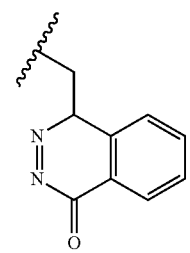

$Z = H, Cl, F, N; n_2 = 0, 1$
$R_4 = NH_2, CH_2NH_2, NHCO(CH_2)_{n3}CH_3, CH_2NHCO(CH_2)_{n3}CH_3, n_3 = 0, 1, 2.$ This derivative is prepared by amidation condensation reaction between an amino group of NICD and a carbonyl group of an aryl isocyanate, a carboxylic acid, or an acid chloride, or symmetrical amidation condensation reaction between an NICD and an aromatic amino group by solid phosgene. This derivative has anti-cancer activity in vivo and in vitro, and may be used for preventing and treating cancer.

11 Claims, 14 Drawing Sheets

(56) References Cited

OTHER PUBLICATIONS

Extended European Search Report issued by European Patent Office dated Oct. 24, 2018 for related European Patent Application No. 18173178.7.
Hefen Sun et al., "Isocorydine Inhibits Cell Proliferation in Hepatocellular Carcinoma Cell Lines by Inducing G2/M Cell Cycle Arrest and Apoptosis", PLoS One, May 2012,vol. 7,Issue 5.
Ping Lu et al., "Isocorydine Targets the Drug-Resistant Cellular Side Population through PDCD4-Related Apoptosis in Hepatocellular Carcinoma", MOLMED,(2012)18:1136-1146.
Lijuan Chen et al., "Derivate isocorydine inhibits cell proliferation in hepatocellular carcinoma cell lines by inducing G2/M cell cycle arrest and apoptosis", Tumor Biol. (2016) 37:5951-5961.
Meng Li et al., "An isocorydine derivative (d-ICD) inhibits drug resistance by downregulating IGF2BP3 expression in hepatocellular carcinoma", Oncotarget,vol. 6, No. 28 (2015).
Binhua Li et al., "Discovery of N-((1-(4-(3-(3-((6,7-Dimethoxy quinolin-3-yl)oxy)phenyl)ureido)-2-(trifluoromethyl)(phenyl)piperidin-4-yl)methyl)propionamide(CHMFL-KIT-8140) as a Highly Potent Type II Inhibitor Capable of Inhibiting the T670I "Gatekeeper" Mutant of cKIT Kinase", Journal of Medicinal Chemistry,(2016) 59:8456-8472.
Qian Yan et al., "Design, synthesis, and anticancer properties of isocorydine derivatives", Bioorganic & Medicinal Chemistry, (2017) 25: 6542-6553.

\* cited by examiner

ISOCORYDINE DERIVATIVES, PREPARATION METHOD AND USE THEREOF

TECHNICAL FIELD

The present invention relates to a chemical structure derivative of a natural product and belongs to the field of synthetic organic chemistry. Particularly, the invention relates to a chemical structure derivative of isocorydine, its preparation method and use thereof.

BACKGROUND ART

Aporphine alkaloids are present in more than 100 plants from more than 20 families and are important secondary metabolites of plants. This type of compounds typically has significant pharmacological activities, such as anti-oxidation, anti-platelet-aggregation, anti-convulsion, anti-spasm, anti-malaria, anti-protozoa, anti-poliovirus, cytotoxicity, anti-Parkinson's disease, and the like. Isocorydine is a typical aporphine alkaloid, and is widely distributed in plants, such as *Dicranostigma leptopodum* (see ZL201310107231.8), *Dactylicapnos scandens, Stephania epigaea, Corydalis yanhusuo, Nandina domestica, Stephania brachyandra, Coptis chinensis, Bergenia purpurascens*, and the like.

It has been indicated by researches that isocorydine can remarkably reduce the proportion of CD133$^+$ positive or EpCAM labeled tumor stem cells and can significantly reduce the spherization and the clonogenicity of CD133$^+$ cells. It has been revealed by researches in vivo that isocorydine may reduce the tumorigenicity of CD133$^+$, isocorydine may significantly reduce the proportion of side population cells in hepatocellular carcinoma cell (HCC) lines, and significantly downregulate the expression of a drug-resistant protein ABCG2 in a dose-dependent manner. It has been demonstrated by tumor xenograft models that isocorydine can selectively reduce the volume and the weight of a tumor induced by side population cells in vivo. It has been indicated by combinated therapy that isocorydine may enhance the drug sensitivity of HCC strains to doxorubicin and plays a role in the reversion of drug resistance. It has been indicated by researches that isocorydine has an activity of targeting HCC side population cells and HCC stem cells and has an activity of reversing drug resistance and is a very potential chemotherapeutic drug for treating hepatocellular carcinoma. (Sun H F, Hou H L, Lu P, et al. Isocorydine inhibits cell proliferation in hepatocellular carcinoma cell cines by inducing G2/M cell cycle arrest and apoptosis. PLoS ONE, 2012, 7(5): e36808; Lu P, Sun H F, Zhang L X, et al. Isocorydine targets the drug-resistant cellular side population through PDCD4-related apoptosis in hepatocellular carcinoma. Mol Med, 2012, 18(7): 1136-1146.). However, isocorydine has a limited inhibition activity for tumor growth of various HCC, and IC$_{50}$ values are all greater than 200 μM. Therefore, with respect to 8-amino-isocorydine (named as NICD in this patent application, see ZL 201210340250.0), which is obtained by performing chemical structure derivation and anti-cancer activity screening researches by the applicant of the patent, the anti-cancer activity is greatly improved. It has been indicated by researches that NICD may selectively act on key targets of tumor cells such as IGF2BP3, GADD45A, and the like and tumor stem cells labeled with CD133$^+$ and may downregulate the expression of drug-resistant drug pump proteins ABCG2 and ABCB1 at the same time, has multi-drug resistance reversion effect and synergistic effect with sorafenib, and has the prospect of new drug development. The applicant of the patent has established relationships between multi-drug resistance of tumor, tumor stem cells, and metastasis and invasion of tumor by the targeted intervention of NICD for the first time, making it possible to solve three core problems in the treatment of hepatocellular carcinoma by one drug. (Chen L J, Tian H, Li M, et al. Derivate isocorydine inhibits cell proliferation in hepatocellular carcinoma cell lines by inducing G2/M cell cycle arrest and apoptosis, Tumour Biol, 2016, 37: 5951-5961; Li M, Zhang L X, Ge C, et al, An isocorydine derivative (d-ICD) inhibits drug resistance by downregulating IGF2BP3 expression in hepatocellular carcinoma. Oncotarget, 2015, 6(28): 25149-25160.). However, in view of the objective presence of the chemical structure fragment of p-aminophenol in the chemical structure of NICD, it results in that NICD cannot be stored in an aqueous solution for a long period, otherwise it will be easily oxidized and degraded and there is a defect in stability. Additionally, compared to modern targeted anti-cancer drugs, it is possible to further optimize its anti-cancer activity.

Sorafenib (having a structural formula as shown in FIG. 1) is the only multi-target tyrosine kinase inhibitor which has been successfully marketed hitherto, is used for treating hepatocellular carcinoma in late stages in which standard therapies are ineffective or cannot be tolerant, and is a gold standard for the treatment of hepatocellular carcinoma in late stages. Although sorafenib may effectively elongate the overall survival time of an HCC patient (by 2 months), toxic and side effects of drugs, drug resistance, and the like generated after administration will severely influence the quality of life and therapeutic effects. Additionally, its high cost is not affordable for most patients. Compound 35 (having a structural formula as shown in FIG. 1) may be used as a type II inhibitor of a tyrosine kinase receptor protein c-KIT kinase and may effectively inhibit the c-KIT kinase and a T670I mutant of c-KIT, and shows a strong anti-proliferation effect for GISTs cancer cell lines GIST-T1 and GIST-5R. (Li B H, Wang A L, Liu J, et al. Discovery of N ((1-(4-(3-(3-((6,7-Dimethoxyquinolin-3-yl)oxy)phenyl)ureido)-2-(trifluoromethyl)phenyl)piperidin-4-1)methyl) propionamide (CHMFL-KIT-8140) as a highly potent type II inhibitor capable of inhibiting the T670I "Gatekeeper" mutant of cKIT kinase. J Med Chem, 2016, 59(18): 8456-8472.). Olaparib (having a structural formula with reference to FIG. 1) is a selective PARP1/2 inhibitor and is used for treating tumors in which BRCA is mutated, for example, ovarian cancer, thymic cancer, and prostate cancer. Additionally, olaparib has selectivies in inhibiting tumor cells having ATM defects, indicating that olaparib may be used as a potential drug for treating lymphomas in which ATM is mutated.

FIG. 1 Chemical structures of three known compounds

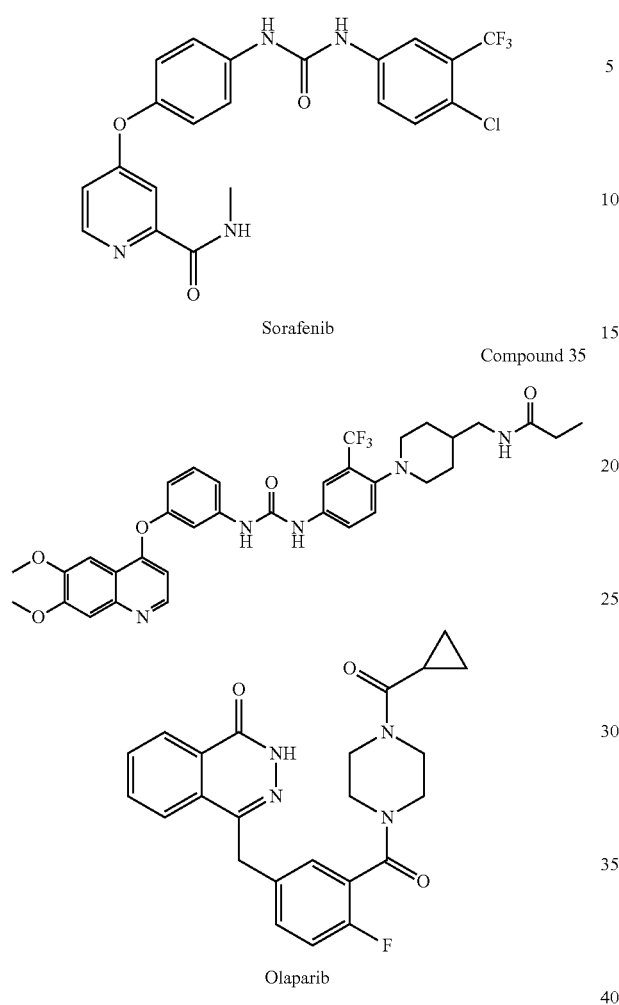

Sorafenib

Compound 35

Olaparib

In light of modern drug design concepts and computer-aided drug design and using molecular docking simulation and optimization, the applicant of the patent has found that when an amino group is introduced at the position C-8 of isocorydine and then chemical structure optimization is further performed on the amino group at C-8, a series of compounds having anti-cancer activities are designed with reference to pharmacophore models of sorafenib, compound 35, and olaparib. The anti-cancer activities of chemical structure derivatives of isocorydine may be significantly improved.

SUMMARY OF THE INVENTION

An objective of present invention is to provide a chemical structure derivative of isocorydine (see formula I). This chemical structure derivative of isocorydine is significantly characterized in that it is generated by substituting the position at C-8 of the mother nucleus of its structure with a chemical group containing nitrogen.

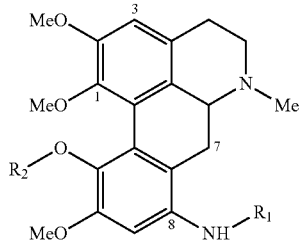

Formula I wherein:
$R_1=$

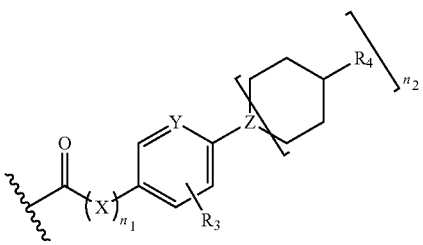

$X=N, C, C=C; n_1=0, 1$
$R_2=H, R_1 Y=C, N$
$R_3=H, Cl, Br, F, CF_3, OCH_3, CH_3,$

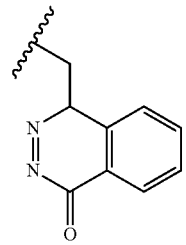 [SMILES: *CC1N=NC(=O)c2ccccc21]

$Z=H, Cl, F, N; n_2=0, 1$
$R_4=NH_2, CH_2NH_2, NHCO(CH_2)_{n_3}CH_3, CH_2NHCO(CH_2)_{n_3}CH_3, n_3=0, 1, 2.$

With respect to the synthesis and preparation method of the isocorydine derivative provided by present invention (formula I), it is synthesized by methods below:

Preparation method 1, wherein preparation is made by performing condensation reaction between NICD and an isocyanate substituted by various aryl groups to form a ureido functional group: an isocyanate is added to an organic solvent solution of NICD to perform condensation reaction with stirring, the reaction solution is added to ice water after the reaction is complete, the solution is adjusted to be basic with an aqueous alkali solution, extraction is performed with dichloromethane, the solvent is recovered, and the product is purified to obtain the compound of interest.

Preparation method 2, wherein preparation is made by performing condensation reaction between NICD and a carboxylic acid or an acid chloride to form an amide functional group: one of a carboxylic acid or an acid chloride is added to an organic solvent solution of NICD, a condensation catalyst is added to perform condensation reaction with stirring, extraction is performed with dichloromethane after the reaction is complete, the solvent is recovered, reactants are purified to obtain the compound of interest.

Preparation method 3, including:

step A, wherein co-condensation reaction is performed between NICD and an aromatic amine in an organic solvent by solid phosgene or phosgene to form a ureido functional group: an arylamine, solid phosgene, and a condensation catalyst are added to an organic solvent solution of NICD to perform condensation reaction with stirring, the solvent is recovered after the reaction is complete, and reactants are purified to obtain the compound of interest;

step B, wherein a reaction product in the step A of the preparation method 3 is dissolved in an organic solvent, an aqueous alkali solution or protic acid is added to perform reaction with stirring, hydrolysis reaction of a protective group is performed, the solvent is recovered after the reaction is complete, and reactants are purified to obtain the compound of interest;

step C, wherein an acid chloride is added to the organic solvent solution of the reaction product in the step B of the preparation method 3, reaction is performed with stirring to form aminoacylation protection, the solvent is recovered after the reaction is complete, and reactants are purified to obtain the compound of interest.

Another objective of present invention is to provide use of the isocorydine derivative and pharmaceutically acceptable salts thereof, particularly as anti-cancer drugs.

Purification methods regarding the synthesized organic compounds in present invention refer to one or more of conventional purification methods for organics which are well known to the person skilled in the art, such as column chromatography purification, liquid-liquid extraction purification, recrystallization, and the like.

The isocyanate in the preparation method 1 of present invention is preferably one of 4-chloro-3-trifluoromethylbenzeneisocyanate, 2,4-dichlorobenzene isocyanate, 4-methylbenzene isocyanate, 4-methylthiobenzene isocyanate, 2-chlorobenzene isocyanate, 2-methylbenzene isocyanate, 4-trifluoromethylbenzene isocyanate, and 4-fluorobenzene isocyanate.

The carboxylic acid or acid chloride in the preparation method 2 of present invention is preferably one of 4-chloro-3-trifluoromethylbenzoic acid, 4-chloro-3-trifluoromethylbenzoyl chloride, trans-cinnamic acid, trans-cinnamoyl chloride, (2E)-4-dimethylamino-2-butenoic acid, (2E)-4-dimethylamino-2-butenoyl chloride, nicotinic acid, nicotinoyl chloride, 5-[(3,4-dihydrogen-4-oxo-1-phthalazinyl)methyl]-2-fluorobenzoic acid, and 4-(4-methyl-1-piperazinylmethyl)-benzoic acid.

The condensation catalyst in the step A of the preparation method 3 of present invention is preferably one of triethylamine, benzotriazole-N,N,N',N'-tetramethyluronium hexafluorophosphate (HBTU), and N,N-diisopropyl ethylamine (DIPEA).

The chemical structures of isocorydine derivatives synthesized by using a chemical structure derivation method in present invention are all demonstrated to be target compounds of interest by various spectroscopic means such as HR-ESI-MS, NMR, and the like.

In present invention, it has been demonstrated by researches on anti-cancer activities in vivo and in vitro that a part of isocorydine derivatives have good anti-cancer activities and may be used as drugs for chemically preventing and treating cancer.

Present invention has following advantages.

Anti-cancer activities in vivo and in vitro of this kind of compounds are relatively greatly improved by modifying the chemical structure of isocorydine; the lipid-water partition coefficient of this type of compounds is improved and the druggability of this type of compounds is improved; and the chemical instability of the structural fragment of p-aminophenol is effectively protected and pharmacokinetic behavior in vivo of this type of compounds is effectively improved, which are favorable to the enhancement of pharmacological activities in vivo of this type of compounds.

The isocorydine derivative synthesized by the directed design has a specified targeting property, particularly for targets on which anti-cancer drugs act, such as Wnt/β-catenin, Ki-67, C-Myc, Vimentin, and the like.

Compound COM33 has an in vivo tumor inhibition rate of up to 73.8% for white Kunming mice bearing $H_{22}$ liver cancer, and does not significantly influence body weight of mice. It is demonstrated that anti-cancer activities in vivo of this kind of compounds may be significantly improved by modifying the chemical structure of isocorydine at the position C-8.

A series of analogs of isocorydine are obtained by structural modification according to present invention and the structural library of aporphine alkaloids are enriched so as to provide a large number of lead compounds for drug screening of this type of compounds.

DESCRIPTION OF EMBODIMENTS

Figure 1:
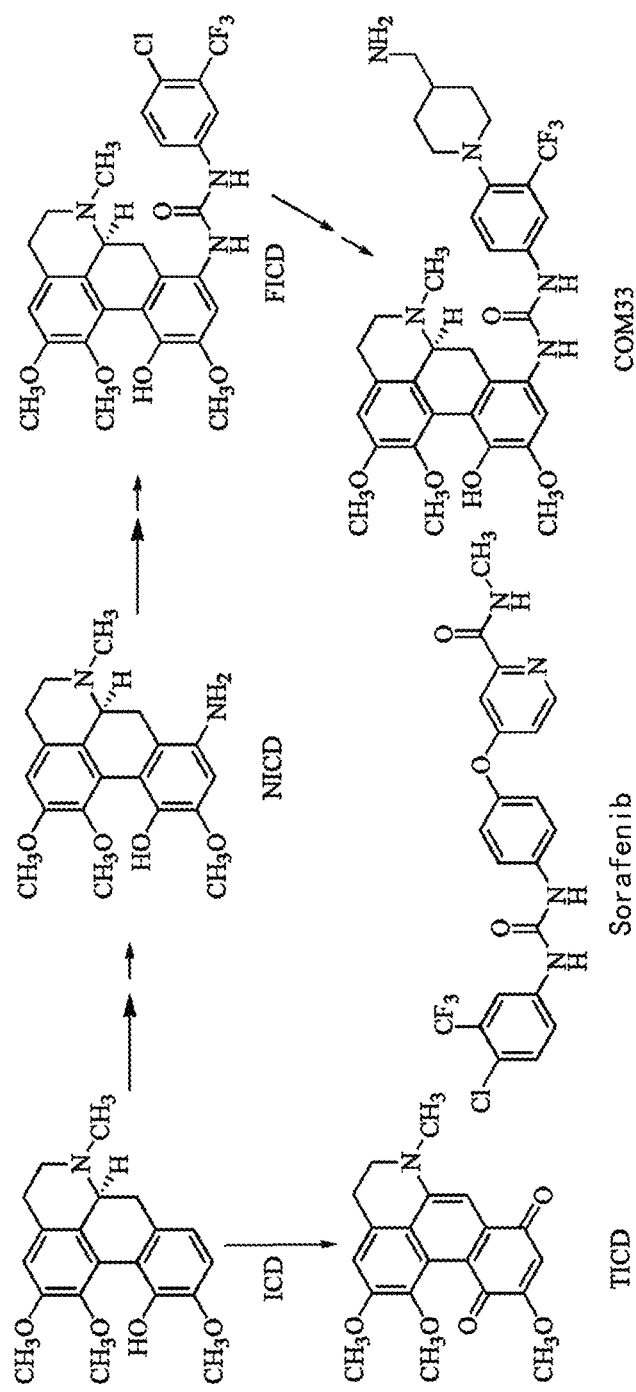
FIG. 1. The chemical structures of main derivatives of isocorydine and the chemical structure of a clinical first-line anti-liver-cancer drug, sorafenib.

In order to better understand present invention, illustration is made by the following Examples, but this patent is not limited to these Examples only.

Example 1

Synthesis of 8-(N-(3'-trifluoromethyl-4'-chloro-phenyl))-ureido-isocorydine (FICD)

A NICD compound (0.7915 g, 2.23 mmol) was dissolved in 50 mL of dichloromethane, and the solution was cooled in ice saline to 0° C. or less. 4-chloro-3-trifluoromethylphenyl isocyanate (0.5822 g, 2.63 mmol) was additionally taken and added to 50 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.9278 g of the compound of interest, FICD, with a yield of 72.3%. The compound was characterized by techniques of MS and NMR to be the target compound.

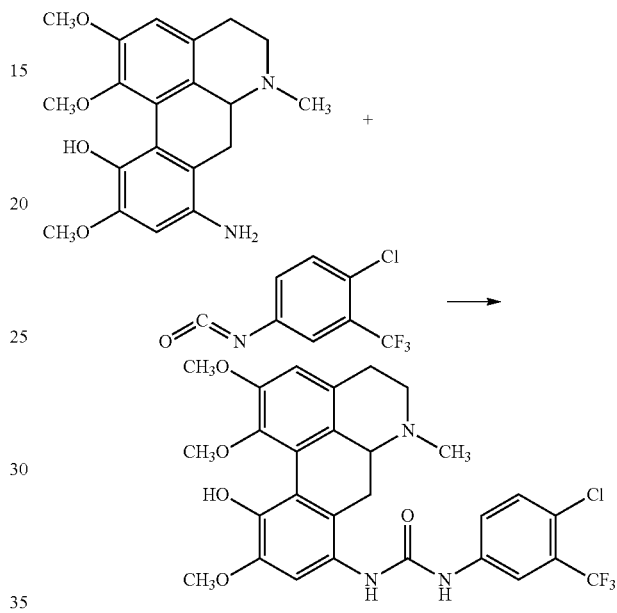

8-(N-(3'-trifluoromethyl-4'-chloro-phenyl))-ureido-isocorydine: a white powder solid. HR-ESI-MS m/z 578.1670 $[M+H]^+$ (calculated for $C_{28}H_{28}ClF_3N_3O_5$: 578.1651), $^1$H-NMR (400 MHz, CDCl$_3$): δ 6.68 (1H, s, H-3), 2.40-2.48 (2H, J=17.2, 2.8 Hz, H-4), 2.68-2.72 (2H, dd, J=17.2, 2.8 Hz, H-5), 2.15 (1H, t, J=14.4, 3.2 Hz, H-6$_a$), 3.38 (1H, d, H-7a), 3.68 (1H, d, H-7b), 7.52 (1H, s, H-9), 2.45 (3H, s, N—CH$_3$), 3.86 (6H, s, 1-OCH$_3$, 2-OCH$_3$), 3.68 (3H, s, 10-OCH$_3$), 7.68 (1H, s, H-2'), 7.34 (1H, d, J=8.0 Hz, H-5'), 7.58 (1H, d, J=8.0 Hz, H-6'); $^{13}$C-NMR (100 MHz, CDCl$_3$): δ 154.1, 152.7, 151.6, 149.6, 145.0, 142.4, 138.0, 137.6, 132.2, 131.8, 131.8, 126.4, 125.2, 124.8, 123.2, 122.9, 122.3, 117.1, 112.5, 111.6, 62.2, 61.4, 56.2, 55.9, 52.5, 43.9, 29.7, 28.6.

Example 2

Synthesis of 8-(N-(3',4'-dichloro-phenyl))-ureido-isocorydine

A NICD compound (0.0906 g, 0.25 mmol) was dissolved in 50 mL of dichloromethane, and the solution was cooled in ice saline to 0° C. or less. 3,4-dichlorophenyl isocyanate (0.0480 g, 0.25 mmol) was additionally taken and added to 50 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.0825 g of the compound of interest, 8-(N-(3',4'-dichloro-phenyl))-ureido-isocorydine, with a yield of 46.9%. The compound was characterized by techniques of MS and NMR to be the target compound.

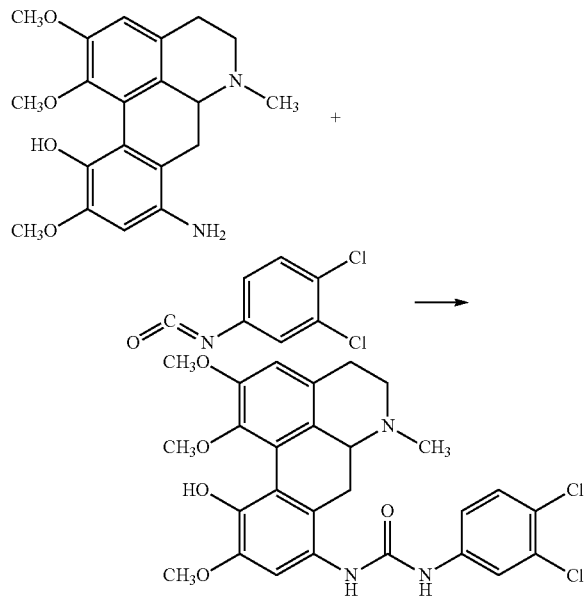

8-(N-(3',4'-dichloro-phenyl))-ureido-isocorydine: a brown powder solid. HR-ESI-MS m/z 544.1386 [M+H]+ (calculated for $C_{27}H_{28}Cl_2N_3O_5$: 544.1401), $^1$H-NMR (400 MHz, CDCl$_3$): δ 6.70 (1H, s, H-3), 2.20-2.26 (2H, J=17.2, 2.8 Hz, H-4), 2.66-2.80 (2H, dd, J=17.2, 2.8 Hz, H-5), 2.15 (1H, t, J=14.0, 3.2 Hz, H-6$_a$), 3.22 (1H, d, H-7a), 3.43 (1H, d, H-7b), 7.60 (1H, s, H-9), 2.52 (3H, s, N—CH$_3$), 3.89 (6H, s, 1-OCH$_3$, 2-OCH$_3$), 3.70 (3H, s, 10-OCH$_3$), 7.20 (1H, s, H-2'), 7.26-7.28 (2H, m, H-5', H-6'); $^{13}$C-NMR (100 MHz, CDCl$_3$): δ 154.1, 151.5, 149.5, 143.2, 142.4, 138.2, 132.6, 130.4, 129.8, 128.4, 128.3, 126.2, 125.3, 125.2, 121.1, 120.9, 118.7, 111.6, 110.6, 62.4, 62.2, 56.2, 55.9, 52.5, 43.5, 29.7, 28.8.

Example 3

Synthesis of 8-(N-p-methylphenyl)-ureido-11-O-p-methylbenzoyl-isocorydine

A NICD compound (0.3032 g, 0.85 mmol) was dissolved in 50 mL of dichloromethane, and the solution was cooled in ice saline to 0° C. or less. 4-tolyl isocyanate (0.1137 g, 0.85 mmol) was additionally taken and added to 50 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.1628 g of the compound of interest, 8-(N-p-methylphenyl)-ureido-11-O-p-methylbenzoyl-isocorydine, with a yield of 30.7%. The compound was characterized by techniques of MS and NMR to be the target compound.

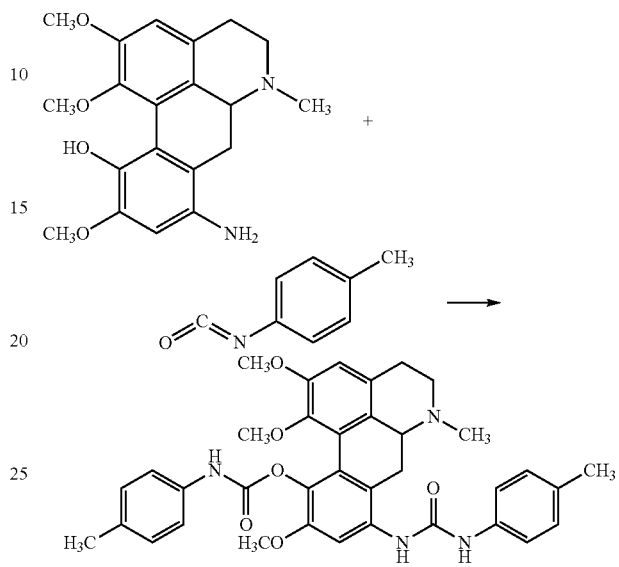

8-(N-p-methylphenyl)-ureido-11-O-p-methylbenzoyl-isocorydine: a brown powder solid. HR-ESI-MS m/z 645.2645 [M+Na]+ (calculated for $C_{36}H_{38}N_4NaO_6$: 645.2684), $^1$H-NMR (400 MHz, CDCl$_3$): δ 7.55-7.40 (m, 2H), 7.33 (s, 2H), 7.28 (s, 1H), 7.13 (d, J=8.0 Hz, 2H), 6.93 (d, J=8.0 Hz, 2H), 6.61 (s, 1H), 3.87-3.80 (m, 4H), 3.68 (dd, J=14.0, 2.4 Hz, 6H), 3.08 (s, 2H), 3.05 (d, J=2.4 Hz, 1H), 2.99 (s, 1H), 2.79 (d, J=14.0 Hz, 3H), 2.47 (s, 3H), 2.35 (s, 3H), 2.29 (s, 3H), 1.99 (s, 1H); $^{13}$C-NMR (101 MHz, CDCl$_3$): δ 153.3, 150.9, 150.1, 145.1, 136.8, 134.8, 133.9, 133.6, 132.8, 131.4, 129.6, 129.0, 127.8, 126.3, 126.2, 123.3, 120.2, 118.7, 112.4, 107.7, 62.2, 61.2, 56.0, 55.5, 52.6, 43.9, 28.7, 26.9, 20.9, 20.7.

Example 4

Synthesis of 8-(N-(4'-methyl sulfide-phenyl))-ureido-isocorydine

A NICD compound (0.1425 g, 0.40 mmol) was dissolved in 50 mL of dichloromethane, and the solution was cooled in ice saline to 0° C. or less. 4-methylthiophenyl isocyanate (0.072 g, 0.41 mmol) was additionally taken and added to 50 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.0920 g of the compound of interest, 8-(N-(4'-methyl sulfide-phenyl))-ureido-isocorydine, with a yield of 43.9%.

The compound was characterized by techniques of MS and NMR to be the target compound.

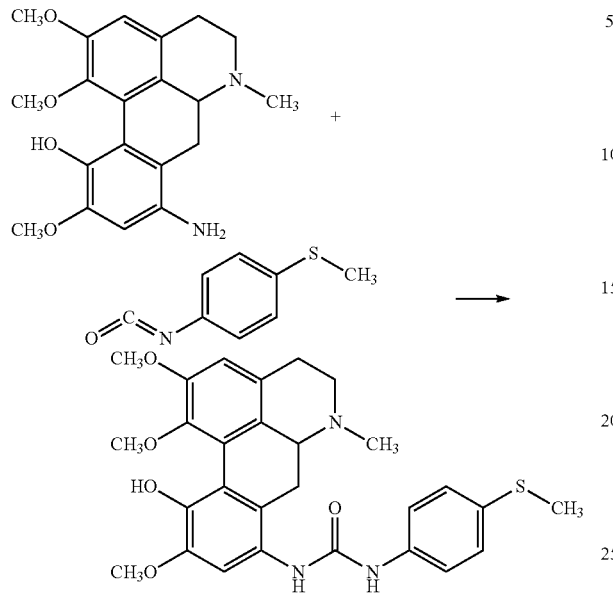

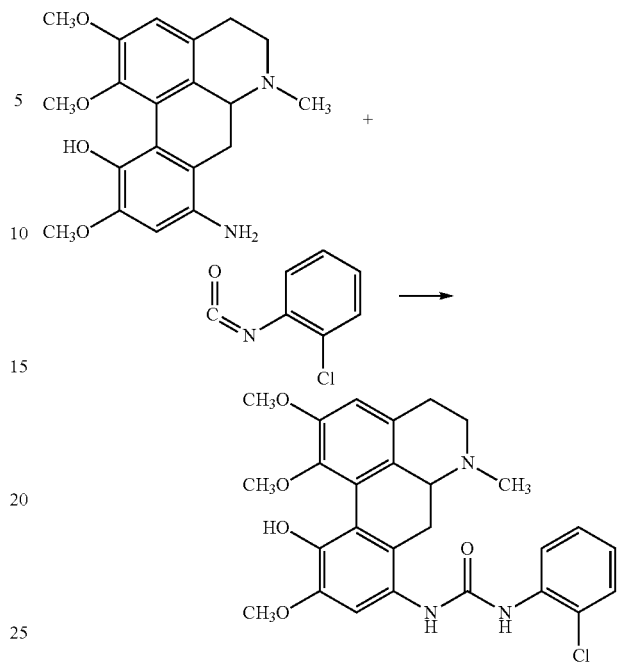

8-(N-(4'-methyl sulfide-phenyl))-ureido-isocorydine: a brown powder solid. HR-ESI-MS m/z 522.2066 [M+H]$^+$ (calculated for $C_{28}H_{32}N_3O_5S$: 522.2057), $^1$H-NMR (400 MHz, CDCl$_3$): $^1$H-NMR (400 MHz, CDCl$_3$): δ 7.16 (d, J=8.0 Hz, 2H), 7.08 (d, J=8.0 Hz, 2H), 6.96 (s, 1H), 6.69 (s, 1H), 3.88 (s, 3H), 3.83 (s, 3H), 3.65 (s, 3H), 3.33 (d, J=16.0 Hz, 1H), 3.18-3.04 (m, 1H), 2.95 (dd, J=11.2, 5.6 Hz, 1H), 2.70 (d, J=8.0 Hz, 2H), 2.37 (s, 3H), 2.36 (s, 3H), 2.07 (d, J=8.0 Hz, 2H); $^{13}$C-NMR (101 MHz, CDCl$_3$): δ 154.7, 151.4, 149.4, 142.9, 142.3, 136.1, 132.5, 129.8, 128.7, 128.3, 125.7, 125.4, 120.9, 120.6, 111.5, 110.5, 62.3, 62.2, 60.4, 56.2, 55.9, 52.5, 43.5, 29.7, 28.9, 16.8.

Example 5

Synthesis of 8-(N-(2'-dichloro-phenyl))ureido-isocorydine

A NICD compound (0.1039 g, 0.29 mmol) was dissolved in 50 mL of dichloromethane, and the solution was cooled in ice saline to 0° C. or less. 2-chlorophenyl isocyanate (0.30 mL, 0.51 mmol) was additionally taken and added to 20 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.0116 g of the compound of interest, 8-(N-(2'-dichloro-phenyl))-ureido-isocorydine, with a yield of 3.9%. The compound was characterized by techniques of MS and NMR to be the target compound.

8-(N-(2'-dichloro-phenyl))ureido-isocorydine: a brown powder solid. HR-ESI-MS m/z 510.1790 [M+H]$^+$ (calculated for $C_{27}H_{29}ClN_3O_5$: 510.1790); $^1$H-NMR (400 MHz, CDCl$_3$): δ 7.32-7.22 (m, 3H), 7.02 (s, 1H), 6.95 (td, J=8.0, 2.0 Hz, 1H), 6.75 (s, 1H), 4.14 (dd, J=16.0, 2.0 Hz, 1H), 3.95 (s, 3H), 3.93 (s, 3H), 3.72 (s, 3H), 3.54 (d, J=16.0 Hz, 1H), 3.33-3.21 (m, 1H), 3.12 (d, J=11.2 Hz, 1H), 3.00 (d, J=10.6 Hz, 1H), 2.75 (dd, J=16.0, 2.0 Hz, 1H), 2.58 (s, 3H), 2.30 (t, J=13.6 Hz, 1H), 2.06 (d, J=3.8 Hz, 1H), 1.35-1.21 (m, 2H); $^{13}$C-NMR (101 MHz, CDCl$_3$) δ 154.1, 151.6, 149.9, 142.5, 135.3, 129.5, 128.8, 127.7, 125.4, 125.1, 125.1, 123.4, 122.3, 121.1, 120.6, 120.5, 111.6, 111.1, 110.9, 62.5, 62.2, 56.3, 55.9, 52.6, 43.5, 29.7, 29.6.

Example 6

Synthesis of 8-(N-(2'-chloro-phenyl))-ureido-11-O-(2"-chloro-benzoyl)-isocorydine A NICD compound (0.1039 g, 0.29 mmol) was dissolved in 50 mL of dichloromethane, and the solution was cooled in ice saline to 0° C. or less. 2-chlorophenyl isocyanate (0.30 mL, 0.51 mmol) was additionally taken and added to 20 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.1661 g of the compound of interest, 8-(N-(2'-chloro-phenyl))-ureido-11-O-(2"-chloro-benzoyl)-isocorydine, with a yield of 43.0%. The compound was characterized by techniques of MS and NMR to be the target compound.

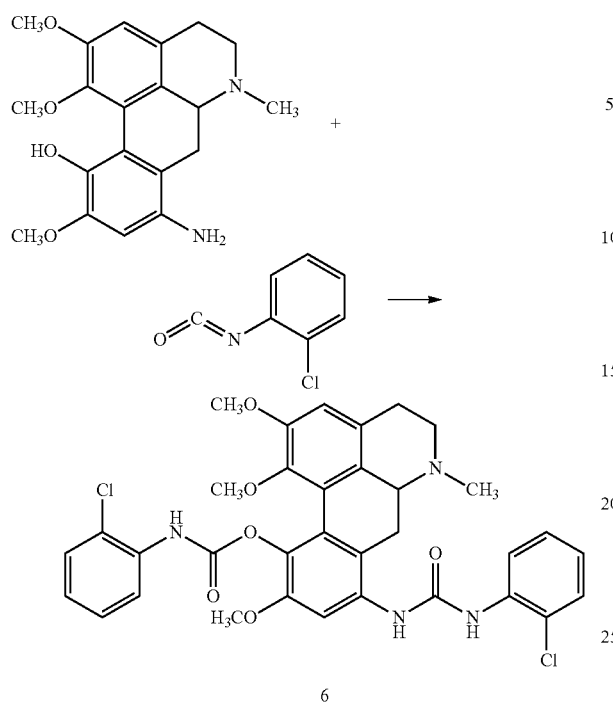

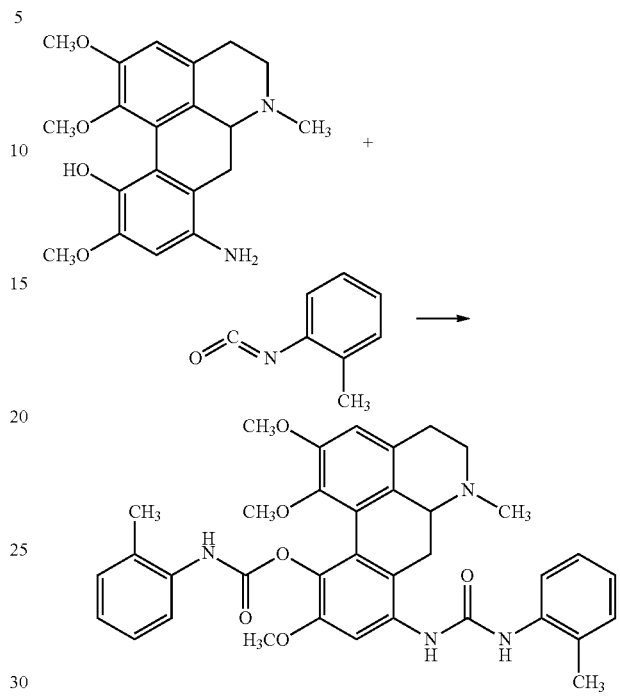

8-(N-(2'-chloro-phenyl))-ureido-11-O-(2"-chloro-benzoyl)-isocorydine: a brown powder solid. HR-ESI-MS m/z 685.1588 [M+Na]$^+$ (calculated for $C_{34}H_{32}Cl_2N_4NaO_6$: 685.1591); $^1$H-NMR (400 MHz, CDCl$_3$): δ 8.12 (s, 1H), 7.65 (s, 1H), 7.40 (d, J=8.0 Hz, 1H), 7.32-7.25 (m, 1H), 7.25-7.10 (m, 4H), 7.01 (t, J=8.0 Hz, 1H), 6.92 (d, J=8.0 Hz, 1H), 6.68 (s, 1H), 3.93 (s, 1H), 3.85 (s, 3H), 3.72 (s, 3H), 3.67 (s, 3H), 3.19 (d, J=12.5 Hz, 1H), 3.03 (dd, J=10.8, 5.2 Hz, 1H), 2.86 (d, J=11.8 Hz, 2H), 2.52 (s, 3H), 2.27-2.09 (m, 2H), 2.07 (s, 1H), 1.28 (t, J=7.1 Hz, 1H); $^{13}$C-NMR (101 MHz, CDCl$_3$): δ 171.2, 152.9, 152.4, 151.5, 150.5, 145.8, 135.9, 134.4, 132.7, 129.3, 129.1, 128.8, 127.8, 127.6, 127.3, 127.0, 124.2, 123.4, 123.2, 122.9, 122.8, 122.5, 120.9, 120.7, 113.4, 107.7, 62.4, 61.2, 60.4, 56.4, 55.9, 52.7, 43.8, 28.5.

dine, with a yield of 61.6%. The compound was characterized by techniques of MS and NMR to be the target compound.

8-(N-(2'-methyl-phenyl))-ureido-11-O-(2"-methyl-benzoyl)-isocorydine: a brown powder solid. HR-ESI-MS m/z 623.2848 [M+H]$^+$ (calculated for $C_{36}H_{39}N_4O_6$: 623.2864); $^1$H NMR (400 MHz, CDCl$_3$): δ 7.28 (s, 2H), 7.21 (s, 4H), 7.05 (t, J=8.0 Hz, 2H), 6.94 (d, J=8.0 Hz, 1H), 6.77 (d, J=8.0 Hz, 1H), 6.58 (s, 1H), 3.78 (d, J=7.2 Hz, 4H), 3.61 (ddd, J=16.0, 2.0, 2.0 Hz, 4H), 3.31-2.82 (m, 6H), 2.57 (s, 3H), 2.26 (d, J=16.0 Hz, 6H), 2.18 (s, 3H), 1.28 (s, 1H); $^{13}$C NMR (101 MHz, CDCl$_3$) δ 153.2, 145.4, 139.1, 138.9, 138.3, 129.0, 128.8, 128.5, 126.2, 125.0, 124.1, 123.3, 122.9, 120.6, 120.3, 119.2, 117.0, 116.8, 115.8, 62.2, 61.3, 55.9, 55.6, 52.6, 46.2, 43.8, 29.8, 28.6.

Example 7

Synthesis of 8-(N-(2'-methyl-phenyl))-ureido-11-O-(2"-methyl-benzoyl)-isocorydine A NICD compound (0.1031 g, 0.29 mmol) was dissolved in 50 mL of dichloromethane, and the solution was cooled in ice saline to 0° C. or less. 2-tolyl isocyanate (0.50 mL, 0.65 mmol) was additionally taken and added to 20 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.1110 g of the compound of interest, 8-(N-(2'-methyl-phenyl))-ureido-11-O-(2"-methyl-benzoyl)-isocory- Example 8

Synthesis of 8-(N-(4'-trifluoromethyl-phenyl))-ureido-isocorydine

A NICD compound (0.1307 g, 0.37 mmol) was dissolved in 50 mL of dichloromethane, and the solution was cooled in ice saline to 0° C. or less. 4-trifluoromethylphenyl isocyanate (0.10 mL, 0.70 mmol) was additionally taken and added to 20 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.0181 g of the compound of interest, 8-(N-(4'-trifluoromethyl-phenyl))-ureido-isocorydine, with a yield of 9.1%. The compound was characterized by techniques of MS and NMR to be the target compound.

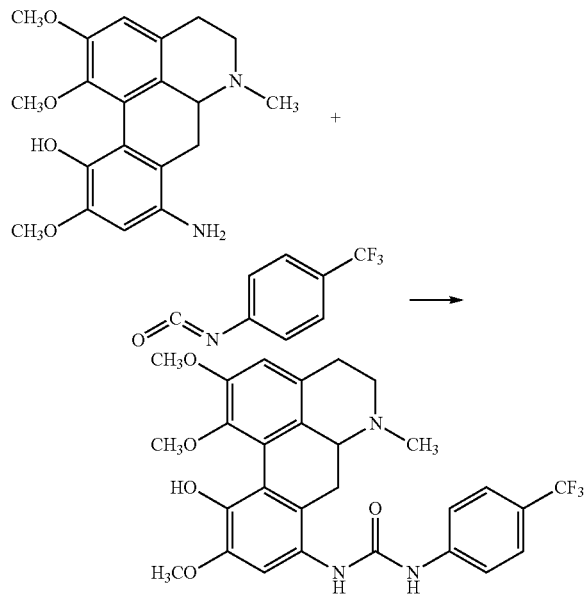

8-(N-(4'-trifluoromethyl-phenyl))-ureido-isocorydine: a brown powder solid. HR-ESI-MS m/z 544.2050 [M+H]+ (calculated for $C_{28}H_{29}F_3N_3O_5$: 544.2054); $^1$H-NMR (400 MHz, CDCl$_3$): δ 7.51 (s, 3H), 7.28 (s, 2H), 7.05 (s, 1H), 6.73 (s, 1H), 3.92 (s, 3H), 3.92 (s, 3H), 3.73 (s, 3H), 3.47 (d, J=14.0 Hz, 1H), 3.24 (m, 1H), 3.09 (m, 1H), 2.93 (m, 1H), 2.75 (d, J=16.0 Hz, 1H), 2.53 (s, 3H), 2.29-2.15 (m, 2H), 1.27 (s, 1H); $^{13}$C-NMR (101 MHz, CDCl$_3$): δ 154.0, 151.7, 149.8, 142.6, 141.8, 136.6, 129.5, 126.2, 126.2, 125.3, 122.9, 121.0, 120.4, 118.6, 111.6, 110.6, 62.6, 62.2, 56.3, 55.9, 52.5, 43.3, 29.7, 29.6.

Example 9

Synthesis of 8-(N-(4'-trifluoromethyl-phenyl))-ureido-11-O-(4''-trifluoromethyl-benzoyl)-isocorydine A NICD compound (0.1307 g, 0.37 mmol) was dissolved in 50 mL of dichloromethane, and the solution was cooled in ice saline to 0° C. or less. 4-trifluoromethylphenyl isocyanate (0.10 mL, 0.70 mmol) was additionally taken and added to 20 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.1193 g of the compound of interest, 8-(N-(4'-trifluoromethyl-phenyl))-ureido-11-O-(4''-trifluoromethyl-benzoyl)-isocorydine, with a yield of 44.5%. The compound was characterized by techniques of MS and NMR to be the target compound.

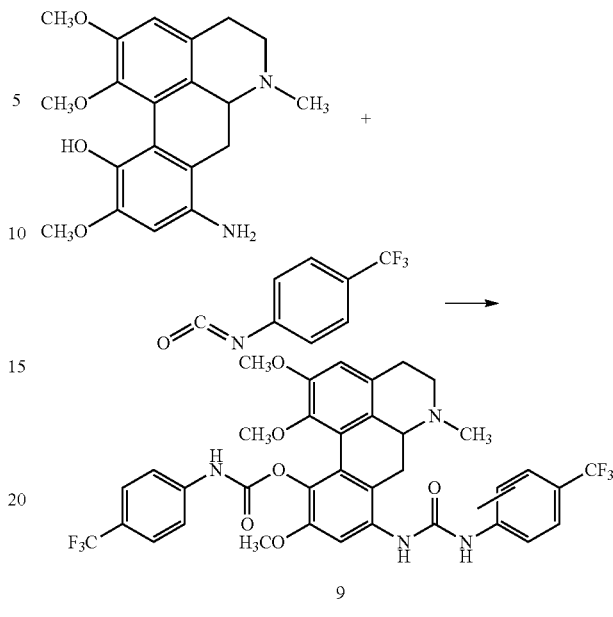

8-(N-(4'-trifluoromethyl-phenyl))-ureido-11-O-(4''-trifluoromethyl-benzoyl)-isocorydine: a brown powder solid. HR-ESI-MS m/z 731.2286 [M+H]+ (calculated for $C_{36}H_{33}F_6N_4O_6$: 731.2299); $^1$H-NMR (400 MHz, CDCl$_3$) δ 7.73 (s, 1H), 7.56 (dd, J=8.0, 2.0 Hz, 4H), 7.37 (d, J=8.0 Hz, 2H), 7.28 (s, 2H), 6.62 (s, 1H), 3.90-3.78 (m, 4H), 3.64-3.49 (m, 6H), 3.04-2.96 (m, 3H), 2.82-2.72 (m, 3H), 2.51 (s, 3H), 2.28-2.19 (m, 2H), 2.13-2.08 (m, 1H); $^{13}$C-NMR (101 MHz, CDCl$_3$) δ 152.7, 151.2, 150.2, 145.1, 142.3, 140.3, 133.5, 132.7, 126.5, 125.9, 125.6, 125.3, 124.4, 124.1, 123.0, 122.9, 122.6, 119.5, 117.9, 112.4, 107.5, 62.1, 61.4, 55.9, 55.7, 52.6, 43.8, 29.7, 28.5.

Example 10

Synthesis of 8-(N-(4'-fluoro-phenyl))-ureido-11-O-(4''-fluoro-benzoyl)-isocorydine A NICD compound (0.1338 g, 0.38 mmol) was dissolved in 50 mL of dichloromethane, and the solution was cooled in ice saline to 0° C. or less. 4-fluorophenyl isocyanate (0.10 mL, 0.70 mmol) was additionally taken and added to 20 mL of dichloromethane to dissolve the compound, cooled to 0° C. or less, dropped into the NICD solution described above with mechanical stirring, and mechanically stirred for 90 min. The endpoint of the reaction was detected with TLC to stop the reaction. The pH value of the reaction solution described above was adjusted with aqueous ammonia, 100×3 mL of dichloromethane were added respectively, extraction was performed for 3 times, organic phases were combined, the organic solvent was recovered, and separation was performed by silica gel column chromatography, wherein petroleum ether:ethyl acetate:methanol=6:2:1, to obtain 0.1527 g of the compound of interest, 8-(N-(4'-fluoro-phenyl))-ureido-11-O-(4''-fluoro-benzoyl)-isocorydine, with a yield of 64.5%. The compound was characterized by techniques of MS and NMR to be the target compound.

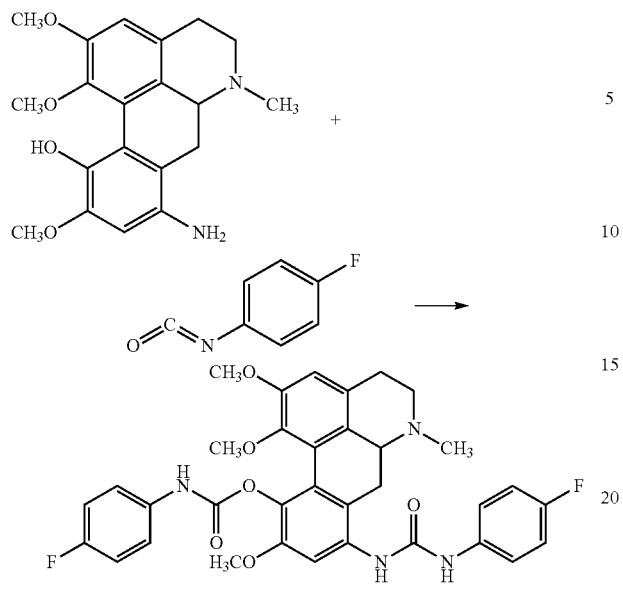
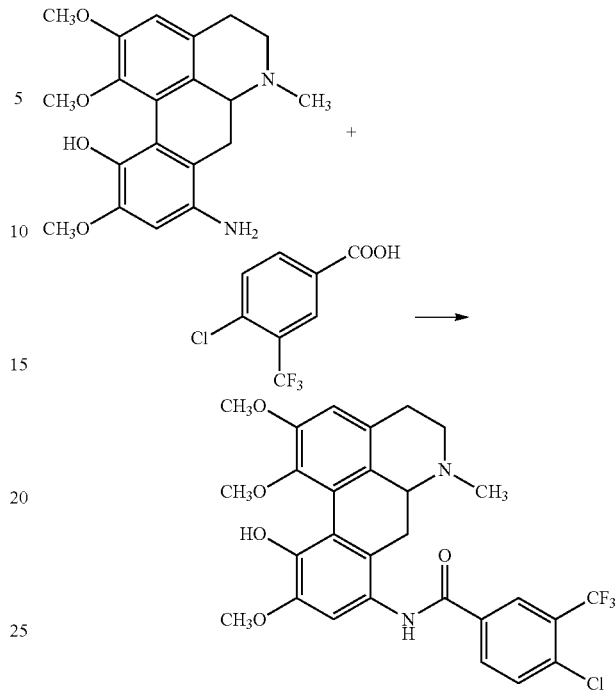

8-(N-(4'-fluoro-phenyl))-ureido-11-O-(4''-fluoro-benzoyl)-isocorydine: a brown powder solid. HR-ESI-MS m/z 631.2354 [M+H]$^+$ (calculated for $C_{34}H_{33}F_2N_4O_6$: 631.2363); $^1$H-NMR (400 MHz, Acetone-d$_6$): δ 7.59 (dt, J=8.0, 2.0 Hz, 5H), 7.07 (dt, J=8.0, 2.0 Hz, 4H), 6.80 (s, 1H), 3.93-3.88 (m, 1H), 3.85 (s, 3H), 3.80 (s, 3H), 3.68 (d, J=6.7 Hz, 1H), 3.45 (s, 3H), 3.36 (dd, J=14.6, 2.7 Hz, 1H), 3.13 (s, 2H), 3.05-2.98 (m, 1H), 2.79 (dd, J=12.5, 3.2 Hz, 1H), 2.68 (dd, J=16.0, 2.0 Hz, 1H), 2.50 (s, 3H), 1.29 (s, 2H); $^{13}$C-NMR (101 MHz, Acetone-d$_6$): δ 151.8, 151.3, 150.1, 148.2, 135.9, 134.3, 133.2, 129.2, 127.9, 124.4, 121.9, 120.1, 115.2, 115.1, 115.0, 114.9, 112.6, 107.5, 62.9, 60.5, 55.6, 55.6, 52.7, 43.3, 30.1, 29.8.

Example 11

Synthesis of 8-N-(3'-trifluoromethyl-4'-chloro-benzoyl)-isocorydine

A NICD compound (0.3573 g, 1.00 mmol) was dissolved in 20 mL of DMF. 4-chloro-3-trifluoromethylbenzoic acid (0.2236 g, 1.00 mmol), HBTU (0.3852 g, 1.02 mmol), and DIPEA (0.1 mL) were additionally taken and added to 50 mL of DMF to dissolve the compound. The NICD solution was added to the above solution with stirring, and mechanically stirred in a water bath at 40° C. for 90 min. The endpoint of the reaction was detected with TLC to stop the reaction. 100×3 mL of dichloromethane were added respectively, extraction was performed for 3 times, and organic phases were combined and concentrated to 100 mL. Extraction was then performed for 3 times with 250×3 mL of distilled water, organic phases were concentrated, the organic solvent was recovered, and separation was performed by silica gel column chromatography, wherein ethyl acetate:methanol=8:1, to obtain 0.3001 g of the compound of interest, 8-N-(3'-trifluoromethyl-4'-chloro-benzoyl)-isocorydine, with a yield of 53.2%. The compound was characterized by techniques of MS and NMR to be the target compound.

8-N-(3'-trifluoromethyl-4'-chloro-benzoyl)-isocorydine: a brown powder solid. HR-ESI-MS m/z 563.1541 [M+H]$^+$ (calculated for $C_{28}H_{27}ClF_3N_2O_5$: 563.1555); $^1$H-NMR (400 MHz, CDCl$_3$): δ7.68 (s, 1H), 7.58 (d, J=8.0, 2.0 Hz, 1H), 7.52 (s, 1H), 7.34 (d, J=8.0 Hz, 1H), 6.68 (s, 1H), 3.86 (s, 6H), 3.68 (s, 3H), 3.58 (m, 1H), 3.38 (m, 1H), 2.68-2.72 (dd, J=16.0, 2.8 Hz, 2H), 2.40-2.48 (dd, J=16.0, 2.8 Hz, 2H), 2.45 (s, 3H), 2.15 (t, J=14.0, 3.2 Hz, 1H); $^{13}$C-NMR (100 MHz, CDCl$_3$): δ 164.1, 152.7, 151.6, 149.6, 145.0, 142.4, 138.0, 137.6, 132.2, 131.8, 131.8, 126.4, 125.2, 124.8, 123.2, 122.9, 122.3, 117.1, 112.5, 111.6, 62.2, 61.4, 56.2, 55.9, 52.5, 43.9, 29.7, 28.6.

Example 12

Synthesis of 8-N-trans-cinnamoyl-isocorydine

A NICD compound (0.3653 g, 1.03 mmol) was dissolved in 20 mL of DMF. Trans-cinnamic acid (0.1914 g, 1.29 mmol), HBTU (0.4397 g, 1.16 mmol), and DIPEA (0.1 mL) were additionally taken and added to 50 mL of DMF to dissolve the compound. The NICD solution was added to the above solution with stirring, and mechanically stirred in a water bath at 40° C. for 90 min. The endpoint of the reaction was detected with TLC to stop the reaction. 100×3 mL of dichloromethane were added respectively, extraction was performed for 3 times, and organic phases were combined and concentrated to 100 mL. Extraction was then performed for 3 times with 250×3 mL of distilled water, organic phases were concentrated, the organic solvent was recovered, and separation was performed by silica gel column chromatography, wherein ethyl acetate:methanol=8:1, to obtain 0.4565 g of the compound of interest, 8-N-trans-cinnamoyl-isocorydine, with a yield of 91.5%. The compound was characterized by techniques of MS and NMR to be the target compound.

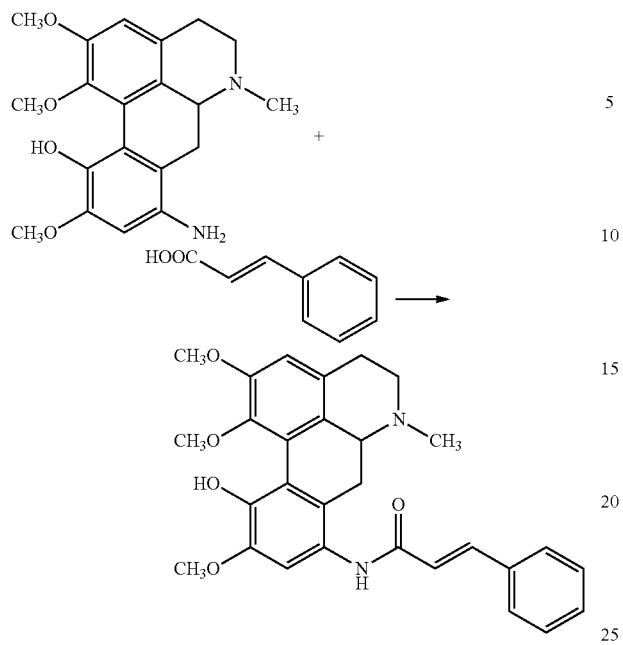

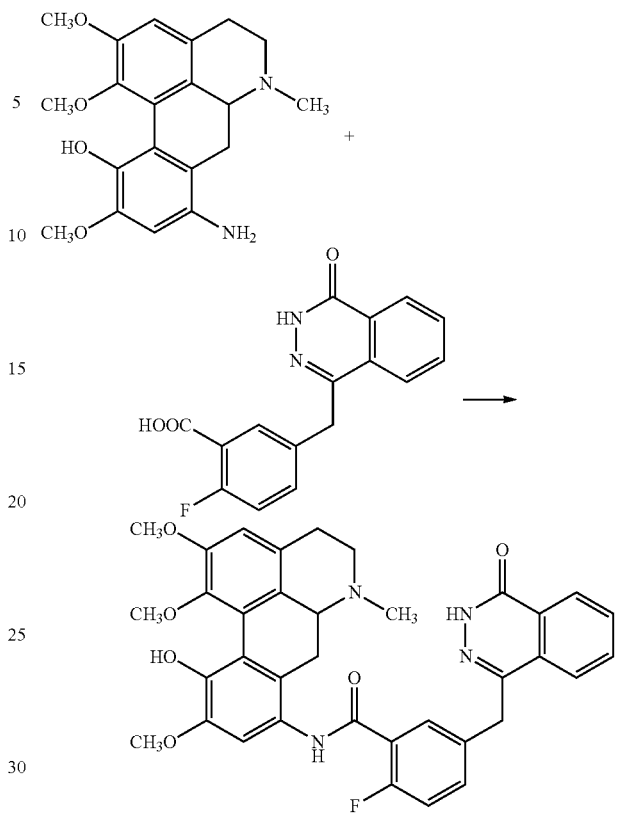

8-N-trans-cinnamoyl-isocorydine had the following spectroscopic data: a brown powder solid. HR-ESI-MS m/z 487.2219 [M+H]$^+$ (calculated for $C_{29}H_{31}N_2O_5$: 487.2227); $^1$H-NMR (400 MHz, Acetone-d$_6$): δ 7.75 (d, J=8.0 Hz, 2H), 7.68 (d, J=16.0 Hz, 1H), 7.61 (dt, J=8.0, 2.0 Hz, 1H), 7.40 (d, J=8.0, 2.0 Hz, 2H), 7.28 (s, 1H), 7.04 (d, J=16.0 Hz, 1H), 6.79 (s, 1H), 4.06 (q, J=7.1 Hz, 1H), 3.86 (s, 3H), 3.84 (s, 3H), 3.66 (s, 3H), 3.42 (dd, J=14.0, 3.4 Hz, 1H), 3.36-3.24 (m, 2H), 2.82 (m, 2H), 2.71 (s, 3H), 2.42 (t, J=14.0 Hz, 1H), 1.29 (s, 1H), 1.20 (t, J=8.0, 2.0 Hz, 1H); $^{13}$C-NMR (101 MHz, Acetone-d$_6$): δ 164.4, 152.0, 148.9, 143.3, 142.9, 142.3, 140.6, 135.2, 129.6, 128.9, 128.6, 128.0, 127.8, 127.01, 125.13, 123.6, 121.9, 118.5, 111.4, 110.4, 110.2, 62.1, 61.3, 59.8, 55.7, 55.4, 52.1, 41.8, 27.3.

Example 13

Synthesis of 8-N-[2-fluoro-5-(4-oxo-3,4-dihydrophthalazin-1-yl)methyl]benzamido isocorydine A NICD compound (0.4186 g, 1.17 mmol) was dissolved in 20 mL of DMF. 2-fluoro-5-(4-oxo-3,4-dihydrophthalazin-1-yl)methylbenzoic acid (0.3090 g, 1.14 mmol), HBTU (0.4495 g, 1.18 mmol), and DIPEA (0.1 mL) were additionally taken and added to 50 mL of DMF to dissolve the compound. The NICD solution was added to the above solution with stirring, and mechanically stirred in a water bath at 40° C. for 90 min. The endpoint of the reaction was detected with TLC to stop the reaction. 100×3 mL of dichloromethane were added respectively, extraction was performed for 3 times, and organic phases were combined and concentrated to 100 mL. Extraction was then performed for 3 times with 250×3 mL of distilled water, organic phases were concentrated, the organic solvent was recovered, and separation was performed by silica gel column chromatography, wherein ethyl acetate:methanol=8:1, to obtain 0.4565 g of the compound of interest, 8-N-[2-fluoro-5-(4-oxo-3,4-dihydrophthalazin-1-yl) methyl]benzamido isocorydine, with a yield of 60.1%. The compound was characterized by techniques of MS and NMR to be the target compound.

8-[2-fluoro-5-(4-oxo-3,4-dihydrophthalazin-1-yl)methyl] benzamido isocorydine had the following spectroscopic data: a brown powder solid. HR-ESI-MS m/z 637.2445 [M+H]$^+$ (calculated for $C_{36}H_{34}FN_4O_6$: 637.2457); $^1$H-NMR (400 MHz, CDCl$_3$): δ 8.46 (d, J=8.0 Hz, 1H), 8.36 (d, J=7.8.0 Hz, 1H), 8.16 (dd, J=7.8, 0.8 Hz, 1H), 7.77 (s, 1H), 7.44-7.39 (d, J=8.0 Hz, 1H), 7.36 (s, 1H), 7.28 (s, 1H), 7.12 (dd, J=8.0, 4.0 Hz, 1H), 6.72 (s, 1H), 4.34 (s, H—N), 3.94 (s, 3H), 3.91 (s, 3H), 3.71 (s, 3H), 3.27 (dd, J=12.0, 4.0 Hz, 1H), 3.23-3.14 (m, 1H), 3.05 (m, 1H), 2.92 (m, 1H), 2.71 (m, 2H), 2.50 (s, 3H), 2.23 (t, J=12.0 Hz, 1H), 2.05 (s, 1H), 1.26 (t, J=8.0 Hz, 1H); $^{13}$C NMR (100 MHz, CDCl$_3$): δ 161.8, 160.8, 160.6, 158.3, 151.4, 149.1, 145.6, 142.6, 142.4, 134.6, 133.7, 132.2, 131.6, 129.7, 129.5, 128.7, 128.3, 127.2, 125.7, 124.9, 123.7, 121.5, 121.3, 120.6, 116.8, 116.5, 111.4, 109.0, 62.2, 56.2, 55.9, 52.6, 43.6, 37.8, 29.7, 28.9.

Example 14

Synthesis of 8-N-nicotinamido-isocorydine

A NICD compound (0.4179 g, 1.17 mmol) was dissolved in 20 mL of DMF. Nicotinic acid (0.1358 g, 1.14 mmol), HBTU (0.4489 g, 1.18 mmol), and DIPEA (0.1 mL) were additionally taken and added to 50 mL of DMF to dissolve the compound. The NICD solution was added to the above solution with stirring, and mechanically stirred in a water bath at 40° C. for 90 min. The endpoint of the reaction was detected with TLC to stop the reaction. 100×3 mL of dichloromethane were added respectively, extraction was performed for 3 times, and organic phases were combined and concentrated to 100 mL. Extraction was then performed for 3 times with 250×3 mL of distilled water, organic phases were concentrated, the organic solvent was recovered, and separation was performed by silica gel column chromatography, wherein ethyl acetate:methanol=8:1, to obtain 0.5462 g of the compound of interest, 8-N-nicotinamido-isocorydine, with a yield of 69.1%. The compound was characterized by techniques of MS and NMR to be the target compound.

organic solvent was recovered, and the extract was separated by silica gel column chromatography to obtain 1.9742 g of 8-N-(phenyl)-ureido-isocorydine, with a yield of 56.1%.

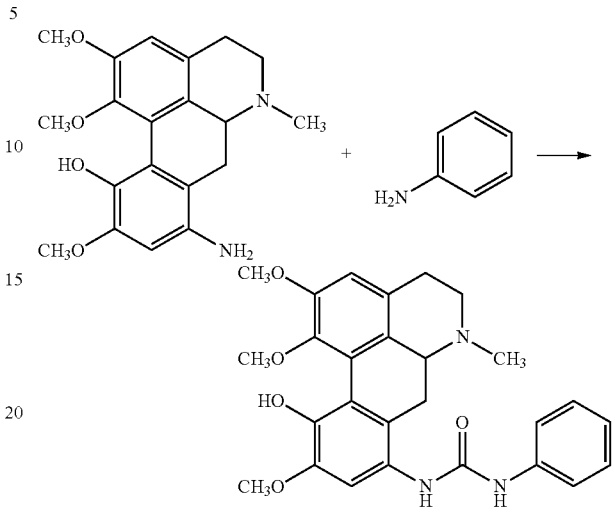

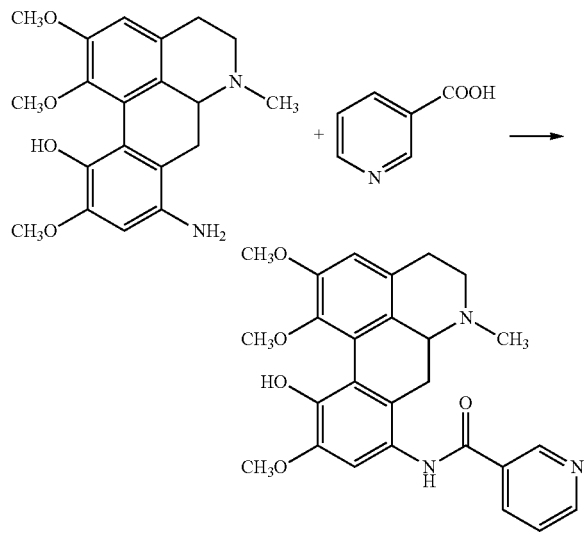

8-(N-phenyl)-ureido-isocorydine had the following spectroscopic data: a brown powder solid. HR-ESI-MS m/z 476.2186 [M+H]$^+$ (calculated for $C_{27}H_{30}N_3O_5$: 476.2180); $^1$H-NMR (400 MHz, CDCl$_3$): δ 7.75 (d, J=8.0 Hz, 1H), 7.75 (d, J=8.0 Hz, 1H), 7.68 (dt, J=8.0, 2.0 Hz, 1H), 7.52 (dt, J=8.0, 2.0 Hz, 1H), 7.40 (t, J=2.0 Hz, 1H), 7.04 (s, 1H), 6.79 (s, 1H), 4.14 (dd, J=14.0, 7.2 Hz, 1H), 3.95 (s, 3H), 3.93 (s, 3H), 3.72 (s, 3H), 3.54 (d, J=14.0 Hz, 1H), 3.33-3.21 (m, 1H), 3.12 (d, J=12.0 Hz, 1H), 3.00 (d, J=12.0 Hz, 1H), 2.75 (dd, J=16.0, 2.4 Hz, 1H), 2.58 (s, 3H), 2.30 (t, J=14.6 Hz, 1H), 2.06 (d, J=4.0 Hz, 1H), 1.35-1.21 (m, 2H); $^{13}$C-NMR (101 MHz, CDCl$_3$) δ 154.1, 151.6, 149.9, 142.5, 135.3, 129.5, 128.8, 127.7, 125.4, 125.1, 125.1, 123.4, 122.3, 121.1, 120.6, 120.5, 111.6, 111.1, 110.9, 62.5, 62.2, 56.3, 55.9, 52.6, 43.5, 29.7, 29.6.

8-N-nicotinamido-isocorydine had the following spectroscopic data: a brown powder solid. HR-ESI-MS m/z 462.2023 [M+H]$^+$ (calculated for $C_{26}H_{28}N_3O_5$: 462.2016); $^1$H-NMR (400 MHz, CDCl$_3$): 7.48 (s, 1H), 7.40 (d, J=8.0 Hz, 1H), 7.31 (s, 1H), 7.07 (d, J=8.0 Hz, 1H), 6.96 (s, 1H), 6.64 (s, 1H), 3.88 (s, 3H), 3.83 (s, 3H), 3.65 (s, 3H), 3.33 (d, J=12.0 Hz, 1H), 3.18-3.04 (m, 1H), 2.95 (m, 1H), 2.70 (m, 2H), 2.37 (s, 3H), 2.36 (s, 3H), 2.07 (m, 2H); $^{13}$C-NMR (101 MHz, CDCl$_3$): δ164.4, 152.0, 148.9, 143.3, 142.9, 142.3, 140.6, 135.2, 129.6, 128.9, 128.6, 128.0, 127.8, 127.01, 125.13, 123.6, 121.9, 118.5, 62.1, 61.3, 59.8, 55.7, 55.4, 52.1, 41.8, 27.3.

Example 15

Synthesis of 8-N-(phenyl)-ureido-isocorydine

A NICD compound (2.3198 g, 6.52 mmol), 4-dimethylaminopyridine (0.0753 g, 0.62 mmol), and triethylamine (1 mL) were dissolved in 200 mL of dichloromethane to obtain a mixed solution of NICD. Solid phosgene (0.7542 g, 2.52 mmol) was dissolved in 50 mL of dichloromethane, the above mixed solution of NICD with stirring was slowly added to a solution of solid phosgene with N$_2$ introduced, and reaction was performed with stirring in an ice water bath at 0° C. for 3 h. 200 mL of dichloromethane, in which aniline (0.5 mL, 5.90 mmol), 4-dimethylaminopyridine (0.0751 g, 0.62 mmol), and triethylamine (1 mL) were dissolved, was then slowly added to above the mixed reaction solution with N$_2$ introduced and with stirring, and reaction was performed with stirring in an ice water bath at 0° C. for 2 h. After completion of dropping, the temperature was increased to room temperature and reaction was performed with stirring for 2 h, and water was then added to quench the reaction. Extraction was performed for 3 times with 300 mL of distilled water, organic phases were concentrated, the Example 16

Synthesis of 8-[3-trifluoromethyl-4-(4-methylaminoformic acid tert-butyl ester)piperidine]benzoylureido isocorydine First step: 2-chloro-5-nitro-trifluorotoluene (0.4106 g, 1.83 mmol) and K$_2$CO$_3$ (0.5078 g, 3.68 mmol) were taken and dissolved in 50 mL of DMF. Piperidine-4-methylaminoformic acid tert-butyl ester (0.3013 g, 1.41 mmol) was then added thereto, stirred at 100° C. for 8 h, and cooled to room temperature after completion of reaction, and the solvent was removed by vacuum. The residue was dissolved in ethyl acetate, extracted for 3 times with 300 mL of water and saline, and dried over MgSO$_4$. Organic phases were concentrated, and the organic solvent was recovered to obtain a crude product of nitrobenzene, which was a yellowish solid. Approximately 0.5 g of the crude product of nitrobenzene was dissolved in 50 mL of a methanol solution, and 0.1324 g of Pd/C palladium on carbon was added. The reaction mixture was stirred in a high-pressure hydrogen reactor at room temperature under a pressure of 0.25 MPa for 3 hours, and filtered by busher funnel after completion of reaction. The filtrate was concentrated, the organic solvent was recovered, and separation was performed by silica gel column chromatography to obtain 0.3124 g of 1-(4-amino-2-(trifluoromethyl)phenyl)piperidine-4-methyl)aminoformic acid tert-butyl ester, with a yield of 59.5%.

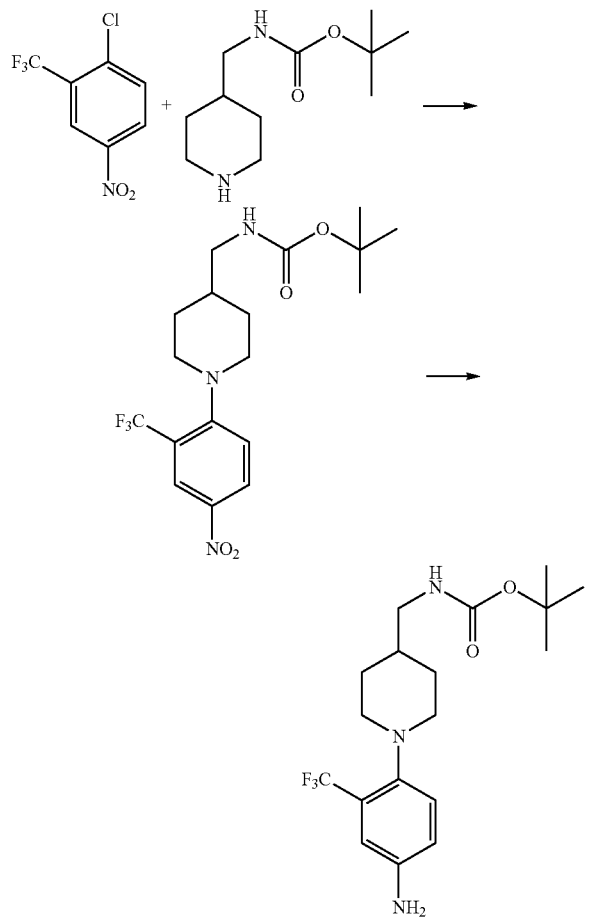

1-(4-amino-2-(trifluoromethyl)phenyl)piperidine-4-methyl)aminoformic acid tert-butyl ester had the following spectroscopic data: an offwhite powder solid. HR-ESI-MS m/z 374.2038 [M+H]$^+$ (calculated for $C_{18}H_{27}F_3N_3O_2$: 374.2050); $^1$H-NMR (400 MHz, CDCl$_3$): δ 7.17 (d, J=8.0 Hz, 1H), 6.92 (d, J=2.0 Hz, 1H), 6.81 (dd, J=8.0, 2.0 Hz, 1H), 4.63 (s, 1H), 3.94 (brs, H N, 1H), 3.06 (t, J=12.0 Hz, 2H), 2.95 (d, J=12.0, 2.0 Hz, 2H), 2.63 (t, J=12.0 Hz, 2H), 1.70 (dd, J=12.0, 2.0 Hz, 2H), 1.45 (s, 9H), 1.38 (dd, J=12.0, 4.0 Hz, 2H), 1.25 (s, 1H); $^{13}$C-NMR (101 MHz, CDCl$_3$): δ 156.1, 144.5, 142.8, 125.3, 118.8, 113.3, 79.10, 54.1, 46.4, 36.2, 30.5, 29.8.

Second step: A NICD compound (2.3235 g, 6.53 mmol), 4-dimethylaminopyridine (0.0753 g, 0.62 mmol), and triethylamine (1 mL) were dissolved in 200 mL of dichloromethane to obtain a mixed solution of NICD. Solid phosgene (0.7537 g, 2.54 mmol) was dissolved in 50 mL of dichloromethane, the above mixed solution of NICD with stirring was slowly added to a solution of solid phosgene with N$_2$ introduced, and reaction was performed with stirring in an ice water bath at 0° C. for 3 h. 200 mL of dichloromethane, in which 1-(4-amino-2-(trifluoromethyl)phenyl)piperidine-4-methyl)aminoformic acid tert-butyl ester (2.1862 g, 5.86 mmol), 4-dimethylaminopyridine (0.0751 g, 0.62 mmol), and triethylamine (1 mL) were dissolved, was then slowly added to above the mixed reaction solution with N$_2$ introduced and with stirring, and reaction was performed with stirring in an ice water bath at 0° C. for 2 h. After completion of dropping, the temperature was increased to room temperature and reaction was performed with stirring for 2 h, and water was then added to quench the reaction. Extraction was performed for 3 times with 300 mL of distilled water, organic phases were concentrated, the organic solvent was recovered, and the extract was separated by silica gel column chromatography to obtain 2.5978 g of 8-(N-(3'-trifluoromethyl-4'-(4"-aminomethyl tert-butyl ester formic acid amide-piperidine)-phenyl))-ureido-isocorydine, with a yield of 58.7%.

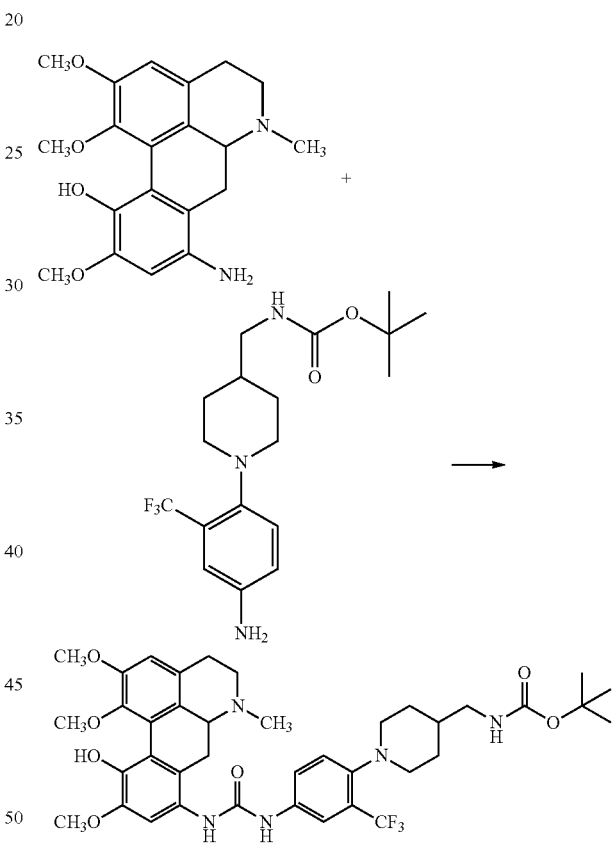

8-(N-(3'-trifluoromethyl-4'-(4"-aminomethyl tert-butyl ester formic acid amide-piperidine)-phenyl))-ureido-isocorydine had the following spectroscopic data: an offwhite powder solid. HR-ESI-MS m/z 756.3571 [M+H]$^+$ (calculated for $C_{39}H_{49}F_3N_5O_7$: 756.3579); $^1$H-NMR (400 MHz, CDCl$_3$): δ 7.50 (d, J=8.0 Hz, 1H), 7.31 (brs, 1H), 7.07 (d, J=8.0 Hz, 1H), 6.96 (s, 1H), 6.64 (s, 1H), 4.83 (s, 1H), 3.83 (s, 3H), 3.76 (s, 3H), 3.58 (s, 3H), 3.26 (d, J=8.0 Hz, 1H), 2.99 (m, 3H), 2.91-2.74 (m, 4H), 2.62 (m, 3H), 2.48 (m, 2H), 2.33 (s, 3H), 2.07-1.95 (m, 1H), 1.62 (m, 2H), 1.42 (s, 9H), 1.36-1.21 (m, 2H). $^{13}$C-NMR (101 MHz, CDCl3): δ 156.4, 154.7, 151.2, 149.1, 148.1, 142.2, 135.5, 129.9, 128.9, 127.6, 127.4, 125.9, 125.4, 125.0, 124.6, 123.6, 122.3, 120.8, 118.1, 111.4, 110.3, 79.3, 63.2, 62.2, 62.1, 56.0, 55.8, 53.8, 52.5, 46.3, 43.5, 37.3, 36.2, 30.4, 29.7, 28.9, 28.4.

Example 17

Synthesis of 8-(N-(3'-trifluoromethyl-4'-(4"-aminomethyl-piperidine)-phenyl))-ureido-isocorydine (COM33)

8-(N-(3'-trifluoromethyl-4'-(4"-aminomethyl tert-butyl ester formic acid amide-piperidine)-phenyl))-ureido-isocorydine (1.4590 g, 1.93 mmol) was dissolved in ethyl acetate (5 mL) containing 4 M HCl and stirred for 1 h, aqueous ammonia was added to adjust the pH value to neutral, and filtration was performed to obtain 1.1618 g of the compound of interest, 8-(N-(3'-trifluoromethyl-4'-(4"-aminomethyl-piperidine)-phenyl))-ureido-isocorydine, with a yield of 91.2%.

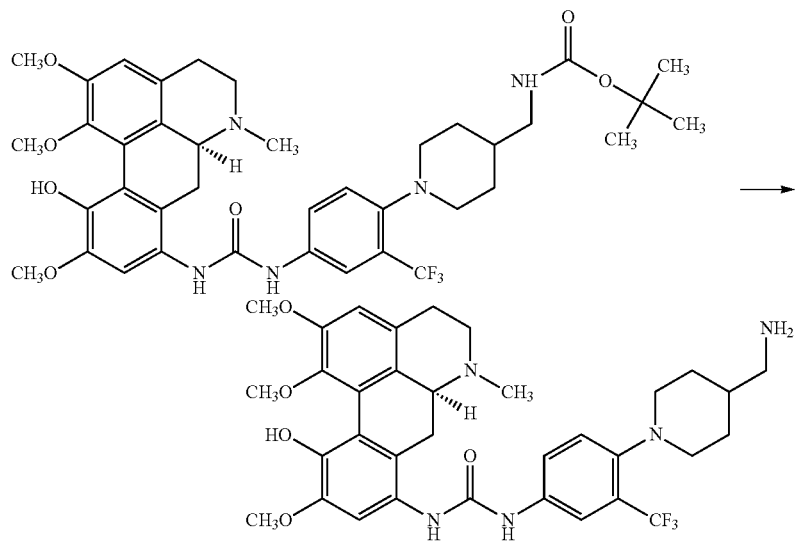

8-(N-(3'-trifluoromethyl-4'-(4"-aminomethyl-piperidine)-phenyl))-ureido-isocorydine had the following spectroscopic data: an offwhite powder solid. HR-ESI-MS m/z 656.3039 [M+H]$^+$ (calculated for $C_{34}H_{41}F_3N_5O_5$: 656.3054); $^1$H-NMR (400 MHz, CD$_3$OD): δ 8.03 (d, J=2.0 Hz, 1H), 7.75 (dd, J=8.0, 2.0 Hz, 1H), 7.67 (d, J=8.0 Hz, 1H), 7.16 (s, 1H), 6.98 (s, 1H), 4.02 (dd, J=12.0, 2.0 Hz, 2H), 3.91 (s, 3H), 3.90 (s, 3H), 3.81-3.75 (m, 2H), 3.71 (s, 3H), 3.58 (dd, J=14.0, 2.0 Hz, 2H), 3.47 (m, 1H), 3.45 (s, 1H), 3.41 (d, J=4.0 Hz, 1H), 3.18 (s, 4H), 3.08 (m, 2H), 2.95 (d, J=8.0 Hz, 3H), 2.52 (t, J=12.0 Hz, 1H), 2.01 (d, J=12.0 Hz, 4H), 1.67 (d, J=10.7 Hz, 2H). $^{13}$C-NMR (101 MHz, CD$_3$OD): δ 156.2, 154.6, 150.3, 145.4, 143.3, 140.4, 128.1, 127.6, 127.0, 126.6, 126.4, 125.7, 124.3, 123.7, 122.7, 120.7, 118.4, 112.6, 111.4, 63.9, 62.3, 56.8, 56.6, 56.2, 53.5, 45.4, 42.4, 34.2, 30.1, 29.0, 26.9.

Example 18

Synthesis of 8-[3-trifluoromethyl-4-(4-methylaminoformic acid propyl ester)-piperidine]benzoylureido isocorydine 8-[3-trifluoromethyl-4-(4-aminomethyl)piperidine]benzoylureido isocorydine (4.1372 g, 6.19 mmol) was dissolved in 60 mL of DMF and dropped into 0.6 mL of newly distilled propionyl chloride, and reaction was performed for 2 h. The reaction solution was pour into 200 mL of ice water, and the pH value of the above reaction product was adjusted to about 8 with aqueous ammonia. Extraction was performed for 3 times with 300 mL of chloroform, organic phases were combined, the organic solvent was recovered, and the extract was separated by silica gel column chromatography to obtain 2.0218 g of 8-[3-trifluoromethyl-4-(4-methylaminoformic acid ethyl ester)-piperidine]benzoylureido isocorydine, with a yield of 48.6%.

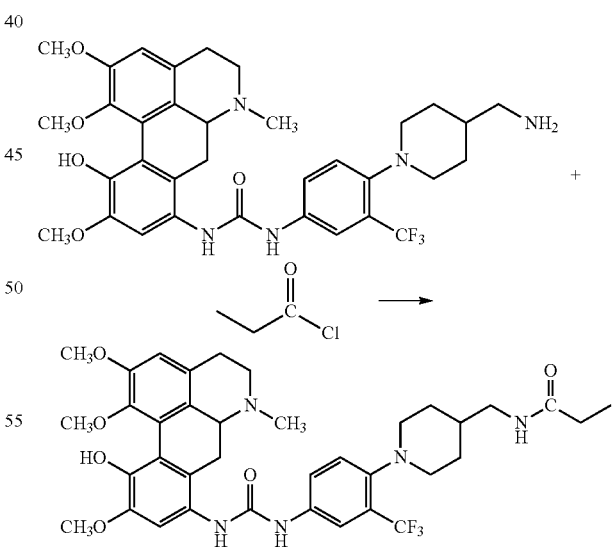

8-[3-trifluoromethyl-4-(4-methylaminoformic acid propyl ester)-piperidine] benzoylureido isocorydine had the following spectroscopic data: an offwhite powder solid. HR-ESI-MS m/z 712.3308 [M+H]$^+$ (calculated for $C_{37}H_{45}F_3N_5O_6$: 712.3322); $^1$H-NMR (400 MHz, DMSO-d$_6$): δ 7.81 (dd, J=8.0, 2.0 Hz, 1H), 7.59 (d, J=2.0 Hz, 1H), 7.34 (d, J=8.0

Hz, 1H), 7.07 (s, 1H), 6.93 (s, 1H), 3.89 (s, 3H), 3.80 (s, 3H), 3.69 (s, 3H), 3.55 (m, 2H), 3.44 (dd, J=14.0, 2.0 Hz, 2H), 2.65 (d, J=3.8 Hz, 1H), 2.41 (s, 3H), 2.35 (s, 1H), 2.24 (d, J=4.0 Hz, 1H), 2.12 (m, 4H), 2.08 (dd, J=14.0, 2.0 Hz, 2H), 1.86 (t, J=6.0 Hz, 3H), 1.67 (t, J=14.0 Hz, 1H), 1.20 (m, 5H), 1.01 (t, J=8.0, 2.0 Hz, 3H). $^{13}$C-NMR (101 MHz, DMSO-$d_6$): δ 173.3, 153.9, 151.5, 148.1, 147.1, 143.1, 141.4, 137.7, 129.4, 127.3, 126.6, 126.3, 125.8, 125.6, 125.3, 123.8, 123.1, 123.0, 120.4, 116.4, 111.9, 109.5, 62.9, 61.7, 56.26, 56.2, 54.1, 52.7, 44.5, 44.1, 40.6, 40.4, 40.2, 40.0, 39.8, 39.6, 39.4, 35.9, 30.8, 30.2, 29.0, 10.6.

Example 19

Synthesis of 8-N-[3'-trifluoromethyl-4'-(4"-aminoformic acid tert-butyl ester-piperidine)-phenyl]-ureido isocorydine First step: 2-chloro-5-nitro-trifluorotoluene (0.4098 g, 1.83 mmol) and K$_2$CO$_3$ (0.5187 g, 3.79 mmol) were taken and dissolved in 50 mL of DMF. Piperidine-4-aminoformic acid tert-butyl ester (0.3047 g, 1.44 mmol) was then added thereto, stirred at 100° C. for 8 h, and cooled to room temperature after completion of reaction, and the solvent was removed by vacuum. The residue was dissolved in ethyl acetate, extracted for 3 times with 300 mL of water and saline, and dried over MgSO$_4$. Organic phases were concentrated, and the organic solvent was recovered to obtain a crude product of nitrobenzene, which was a yellowish solid. Approximately 0.5 g of the crude product of nitrobenzene was dissolved in 50 mL of a methanol solution, and 0.1324 g of Pd/C palladium on carbon was added. The reaction mixture was stirred in a high-pressure hydrogen reactor at room temperature under a pressure of 0.25 MPa for 3 h, and filtered by celite after completion of reaction. The filtrate was concentrated, the organic solvent was recovered, and separation was performed by silica gel column chromatography to obtain 0.3029 g of 1-(4-amino-2-(trifluoromethyl) phenyl)piperidine-4-methyl) aminoformic acid tert-butyl ester, with a yield of 56.9%.

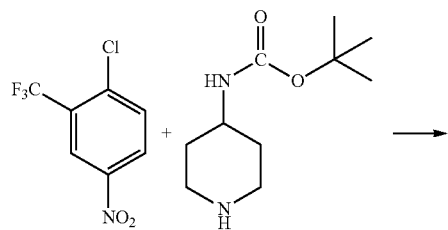

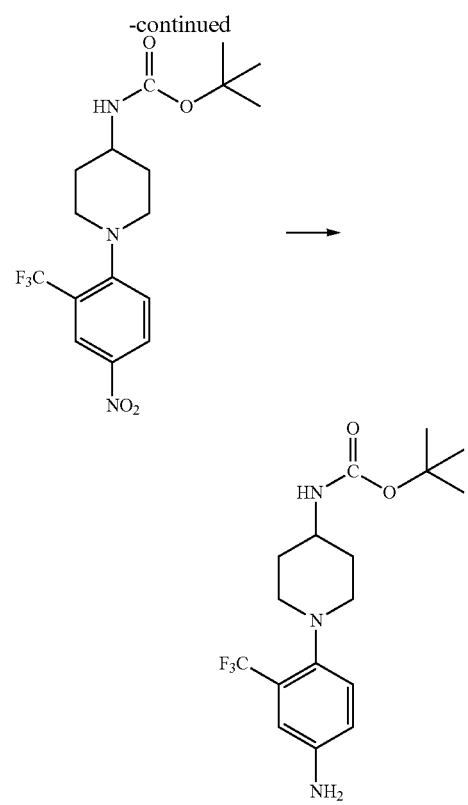

1-(4-amino-2-(trifluoromethyl)phenyl)piperidine-4-aminoformic acid tert-butyl ester had the following spectroscopic data: a yellowish powder solid. HR-ESI-MS m/z 382.1718 [M+Na]+ (calculated for C$_{17}$H$_{24}$F$_3$N$_3$NaO$_2$: 382.1713); $^1$H-NMR (400 MHz, CDCl$_3$): δ 7.15 (d, J=8.0 Hz, 1H), 6.89 (d, J=2.0 Hz, 1H), 6.78 (dd, J=8.0, 2.0 Hz, 1H), 4.54 (s, 1H), 2.90 (d, J=12.0 Hz, 2H), 2.72 (t, J=8.0 Hz, 2H), 1.95 (d, J=12.0 Hz, 2H), 1.54 (ddd, J=14.0, 12.0, 4.0 Hz, 3H), 1.46 (s, 9H). $^{13}$C NMR (101 MHz, CDCl$_3$): δ 155.30, 143.75, 143.51, 125.24, 122.53, 118.59, 113.03, 79.19, 53.06, 47.70, 33.22, 28.43.

Second step: A NICD compound (0.2324 g, 0.65 mmol), 4-dimethylaminopyridine (0.0075 g, 0.06 mmol), and triethylamine (1 mL) were dissolved in 50 mL of dichloromethane to obtain a mixed solution of NICD. Solid phosgene (0.0754 g, 0.25 mmol) was dissolved in 20 mL of dichloromethane, the above mixed solution of NICD with stirring was slowly added to a solution of solid phosgene with N$_2$ introduced, and reaction was performed with stirring in an ice water bath at 0° C. for 3 h. 50 mL of dichloromethane, in which 1-(4-amino-2-(trifluoromethyl) phenyl)piperidine-4-aminoformic acid tert-butyl ester (0.2186 g, 0.57 mmol), 4-dimethylaminopyridine (0.0075 g, 0.06 mmol), and triethylamine (1 mL) were dissolved, was then slowly added to above the mixed reaction solution with N$_2$ introduced and with stirring, and reaction was performed with stirring in an ice water bath at 0° C. for 2 h. After completion of dropping, the temperature was increased to room temperature and reaction was performed with stirring for 2 h, and water was then added to quench the reaction. Extraction was performed for 3 times with 300 mL of distilled water, organic phases were concentrated, the organic solvent was recovered, and the extract was separated by silica gel column chromatography to obtain 0.2568 g of 8-N-[3'-trifluoromethyl-4'-(4"-aminoformic acid tert-butyl ester-piperidine)-phenyl]-ureido isocorydine, with a yield of 58.3%.

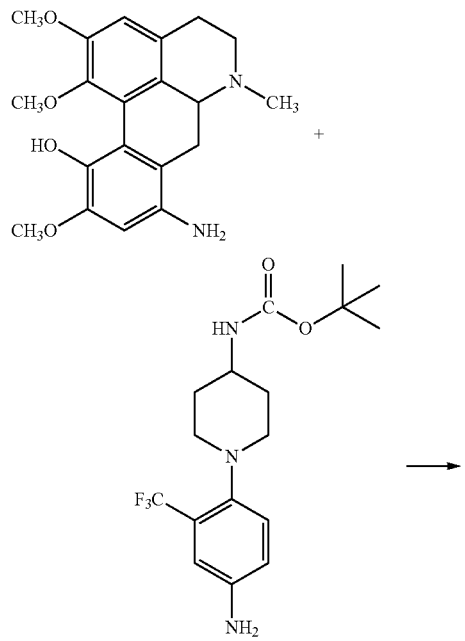

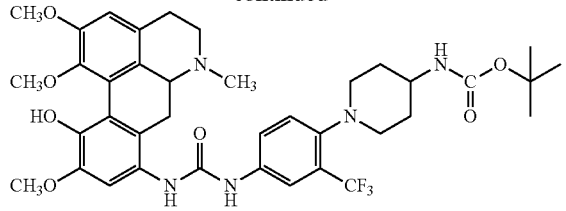

8-N-[3'-trifluoromethyl-4'-(4"-aminoformic acid tert-butyl ester-piperidine)-phenyl]-ureido isocorydine had the following spectroscopic data: a brown powder solid. HR-ESI-MS m/z 742.3430 [M+H]+ (calculated for $C_{38}H_{47}F_3N_5O_7$: 742.3422); $^1$H-NMR (400 MHz, CDCl$_3$): δ 7.51 (s, 1H), 7.40 (dd, J=8.0, 2.0 Hz, 1H), 7.04 (d, J=8.0 Hz, 1H), 6.95 (s, 1H), 6.62 (s, 1H), 4.64 (s, 1H), 3.81 (s, 3H), 3.72 (s, 3H), 3.55 (s, 3H), 3.33 (s, 1H), 3.23 (d, J=12.0 Hz, 2H), 3.04 (s, 2H), 2.81 (m, 4H), 2.60 (m, 4H), 2.31 (s, 3H), 1.99 (t, J=12.0 Hz, 1H), 1.86 (s, 2H), 1.41 (s, 9H). $^{13}$C-NMR (101 MHz, CDCl$_3$) δ 155.5, 154.7, 151.2, 148.9, 147.4, 142.2, 135.9, 129.8, 128.8, 127.6, 127.3, 126.1, 125.4, 125.0, 124.5, 123.4, 122.3, 120.7, 117.9, 111.3, 110.2, 79.3, 62.1, 62.0, 55.9, 55.8, 52.8, 52.4, 50.2, 47.6, 43.4, 33.0, 29.6, 28.9, 28.4.

Example 20

Synthesis of 8-(N-(3'-trifluoromethyl-4'-(4"-aminopiperidine)-phenyl))-ureido-isocorydine 8-(N-(3'-trifluoromethyl-4'-(4"-amino tert-butyl ester formic acid amide-piperidine)-phenyl))-ureido-isocorydine (0.1459 g, 0.19 mmol) was dissolved in ethyl acetate (1 mL) containing 4 M HCl and stirred for 1 h, aqueous ammonia was added to adjust the pH value to neutral, and filtration was performed to obtain 0.1162 g of the compound of interest, 8-(N-(3'-trifluoromethyl-4'-(4"-aminomethyl-piperidine)-phenyl))-ureido-isocorydine, with a yield of 90.6%.

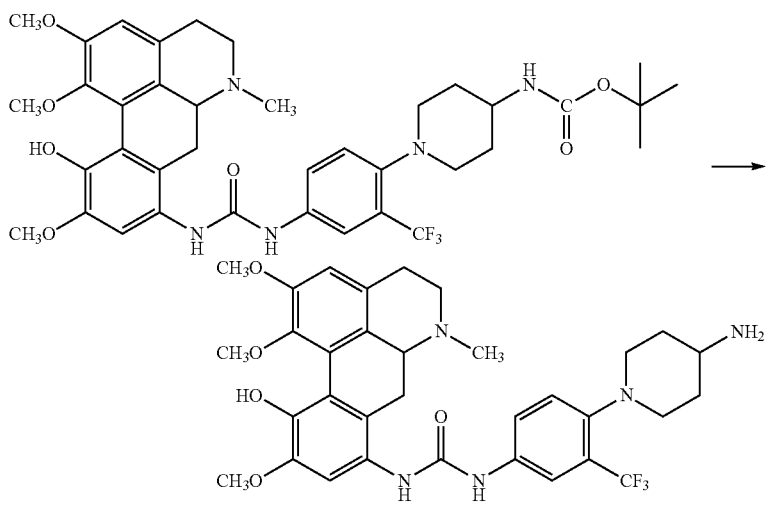

8-(N-(3'-trifluoromethyl-4'-(4"-aminomethyl-piperidine)-phenyl))-ureido-isocorydine had the following spectroscopic data: an offwhite powder solid. HR-ESI-MS m/z 642.2891 [M+H]+ (calculated for $C_{33}H_{39}F_3N_5O_5$: 642.2898); $^1$H-NMR (400 MHz, CDCl$_3$): δ 7.91 (d, J=2.0 Hz, 1H), 7.63 (dd, J=8.0, 2.0 Hz, 1H), 7.44 (d, J=8.0 Hz, 1H), 7.14 (s, 1H), 6.97 (s, 1H), 4.00 (d, J=12.0 Hz, 2H), 3.90 (s, 3H), 3.89 (s, 3H), 3.80-3.72 (m, 2H), 3.70 (s, 3H), 3.61-3.53 (m, 2H), 3.50-3.37 (m, 3H), 3.28-3.21 (m, 2H), 3.17 (s, 3H), 3.11-2.97 (m, 4H), 2.87 (m, 2H), 2.51 (t, J=12.0 Hz, 1H), 2.07 (m, 2H), 1.81 (m, 2H). $^{13}$C NMR (101 MHz, CD$_3$OD) δ 155.0, 153.2, 149.0, 146.0, 144.00, 141.9, 137.3, 126.9, 126.2, 125.3, 124.9, 122.9, 122.6, 122.3, 121.4, 119.3, 116.8, 111.2, 110.1, 68.1, 62.5, 60.9, 55.4, 55.2, 52.2, 51.8, 41.0, 30.5, 29.8, 27.6, 27.4, 25.6.

Example 21

Anti-Cancer Activity Screening Research on Isocorydine Derivatives

By using an MTT method, a sample solution to be tested was added to a 96-well plate in which cancer cells were adherently grown. Culturing was performed for a certain period, and the growth inhibition effect of a compound on a human cancer cell strain for primary screening was measured to determine the anti-cancer activity of the compound. The compound number follows the Example number, and sorafenib was used as a positive control drug.

The specific method was as follows:

1. Human cancer cell strains for activity screening: human cervical cancer Hela cell strains, human liver cancer cell strain HepG2, human gastric cancer cell strain MGC-803, human breast cancer cell strain MAD-MB-231, human liver cancer cell strain SMMC-7721, human brain glioma U251, provided by pre-clinical pharmacological research laboratory, Lanzhou University.

2. Cell culture: A cell incubator was set to conditions of 37° C., 5% $CO_2$, and a saturated humidity, cells were cultured under these conditions, and the cell medium was a DMEM complete medium, wherein 10% fetal bovine serum, 100 IU/mL penicillin, and 100 μg/mL streptomycin were comprised.

3. MTT cell proliferation detection:

3.1. Cancer cells were digested with 0.25% trypsin, centrifuged at 800 rpm for 5 min, and washed to prepare a single cell suspension. The single cell suspension was diluted to $5\times10^3$/100 μL after counting, inoculated on a 96-well cell culture plate (triplicate), and adherently cultured overnight;

3.2. After 24 h of adhesion, the complete medium was discarded, 100 μL-sample-solutions to be tested having different concentrations were sequentially added to the 96-well plate according to a concentration gradient, and incubations were continued for 24 h, 48 h, and 72 h;

3.3. The culture liquid was discarded, a 0.5 mg/mL MTT diluted working liquid was added, and incubation was performed for 4 h by placing in an incubator;

3.4. The culture liquid was discarded, 100 μL of DMSO was added, low-speed oscillation was performed for 10 min by placing on a shaker, and the spectrophotometric value of each well was measured at a wavelength of 490 nm by using a microplate reader. Statistical analysis was performed and tumor cell growth inhibition rate was calculated according to the equation: Growth inhibition rate=(OD value of control group−OD value of experimental group)/OD value of control group.

Results were shown in Table 1.

TABLE 1

Growth inhibition effect ($IC_{50}$: μM) of isocorydine derivatives on 3 strains of cancer cells, HepG2, Hela, and MGC-803.

| Compound * | $IC_{50}$ | | |
|---|---|---|---|
| | HepG2 | HeLa | MGC-803 |
| 1(FICD) | 17.16 | 26.52 | 16.64 |
| 2 | 28.36 | 21.73 | 30.02 |
| 3 | 16.15 | 19.10 | 25.62 |
| 4 | 53.17 | 46.64 | 47.79 |
| 5 | 36.74 | 36.94 | 35.17 |
| 6 | 17.25 | 27.05 | 26.90 |
| 7 | 31.35 | 43.89 | 22.83 |
| 8 | 45.86 | 48.99 | 57.27 |
| 9 | 44.11 | 47.67 | 39.32 |
| 10 | 26.67 | 26.83 | 25.08 |
| 11 | 21.53 | 16.55 | 21.89 |
| 12 | 63.37 | 74.49 | 37.86 |
| 13 | 30.19 | 29.56 | 27.20 |
| 14 | 69.75 | 49.58 | 34.66 |
| 15 | 75.37 | 62.11 | 56.63 |
| 16 | 18.94 | 22.12 | 23.18 |
| 17(COM33) | 7.51 | 6.32 | 11.14 |
| 18 | 10.69 | 12.52 | 10.41 |
| 19 | 25.91 | 26.72 | 28.74 |
| 20 | 18.61 | 13.74 | 22.30 |
| Sorafenib | 15.00 | 12.02 | 19.92 |

* Note:
The Example number corresponds to the compound number.

It can be seen from the above table that compound 1 (FICD), compound 17 (COM33), and compound 18 have relatively better anti-cancer activities, and particularly compound 17 has an $IC_{50}$ lower than 10 μM for all of three types of tumor cells.

Example 22

Growth Inhibition Effect of Isocorydine and Typical Representative Derivatives Thereof on Three Different Types of Tumor Cells According to the MTT method in Example 21, a sample solution to be tested was added to a 96-well plate in which cancer cells were adherently grown. Culturing was performed for a certain period, the growth inhibition effect of a compound on 3 human cancer cell strains for primary screening was measured to determine the anti-cancer activity of the compound, and a growth inhibition curve was plotted. Activity test compounds, chemical structures, and compound designations can be seen in FIG. 1: isocorydine (ICD), 8-amino-isocorydine (NICD), 8-(N-(3'-trifluoromethyl-4'-chloro-phenyl))-ureido-isocorydine (FICD), 8-(N-(3'-trifluoromethyl-4'-(4"-aminomethyl-piperidine)-phenyl))-ureido-isocorydine (COM33), and isocorydione (TICD) as a known compound, and sorafenib was the only molecular targeted therapy drug at present for clinically treating liver cancer in late stages and was used as the positive control drug.

Figure 2:
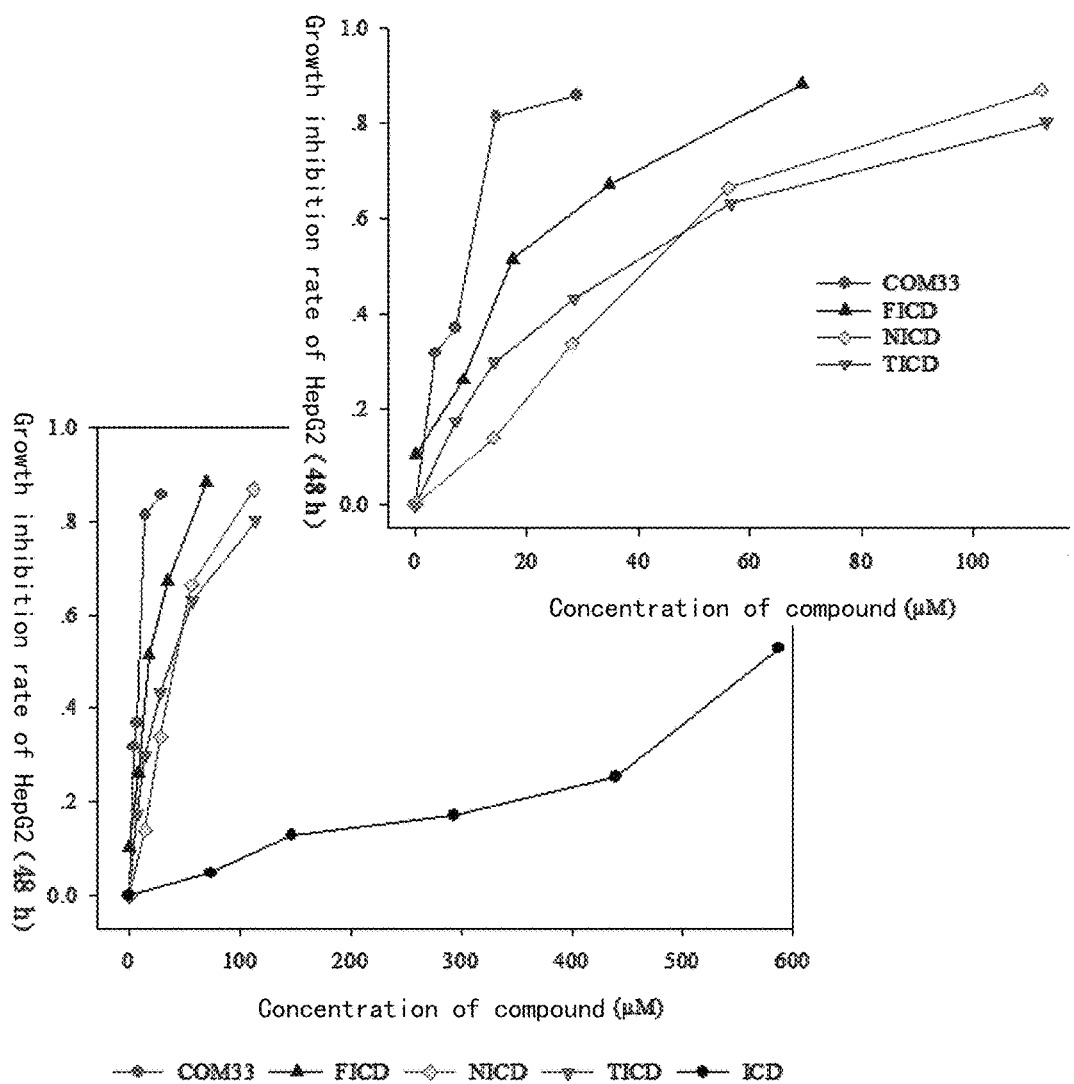
FIG. 2. Growth inhibition effect of isocorydine derivatives on hepatocellular carcinoma cells, which are HepG2 cells.
Figure 3:
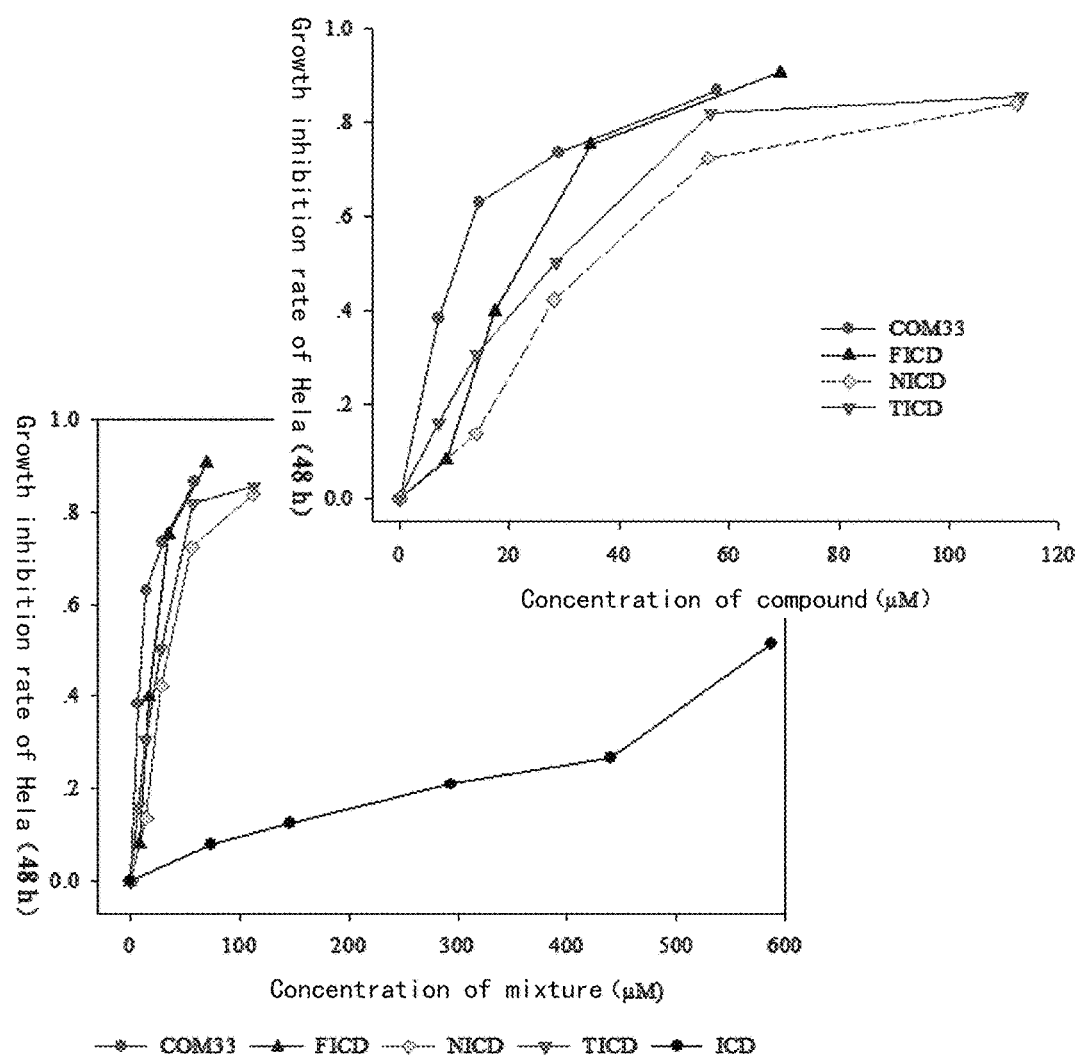
FIG. 3. Growth inhibition effect of isocorydine derivatives on cervical cancer cells, which are Hela cells.
Figure 4:
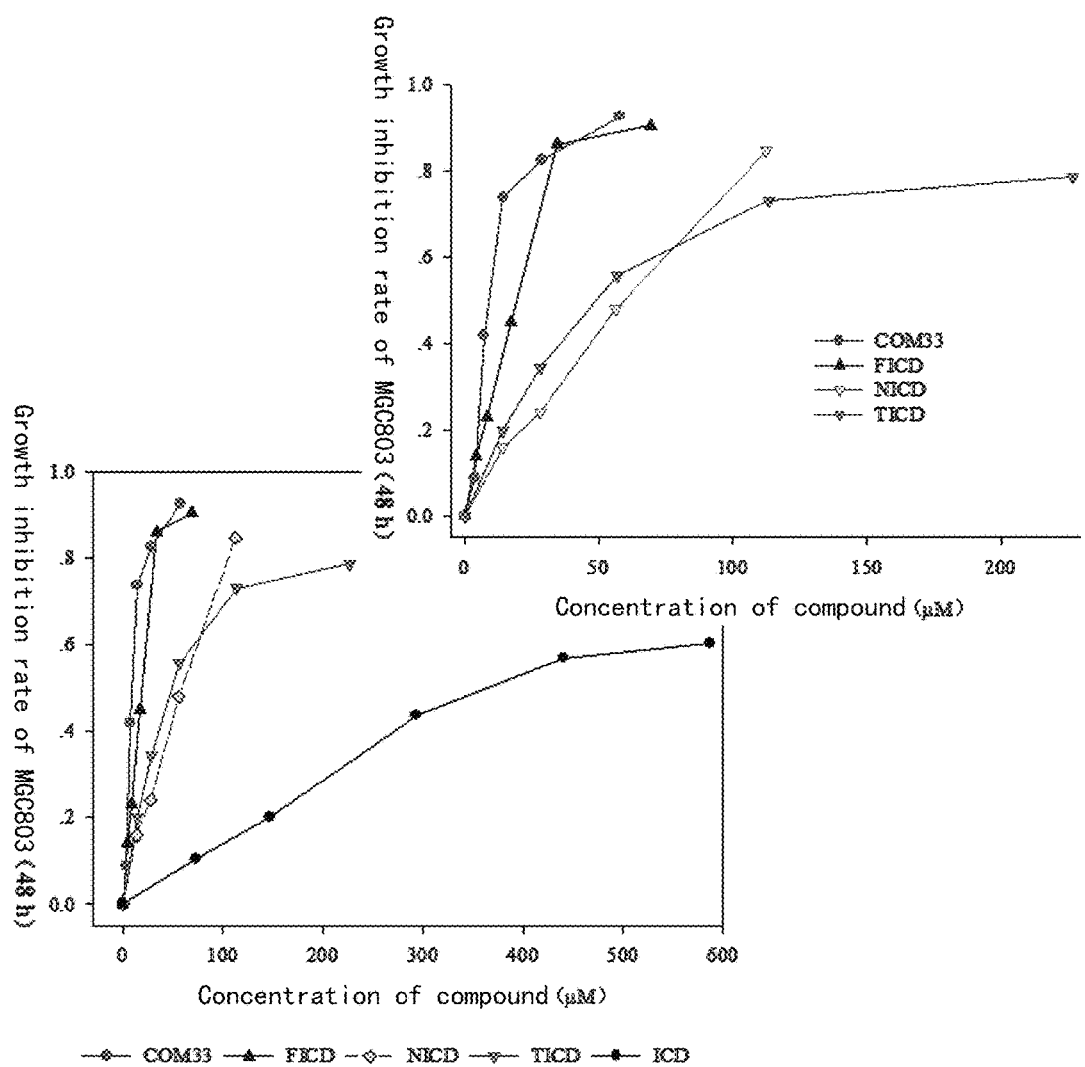
FIG. 4. Growth inhibition effect of isocorydine derivatives on gastric cancer cells, which are MGC-803 cells.

Results can be seen in Table 2, as well as FIG. 2, FIG. 3, and FIG. 4.

TABLE 2

Growth inhibition effect ($IC_{50}$: μM) of isocorydine derivatives on 3 strains of cancer cells, HepG2, Hela, and MGC-803.

| Compound | HepG2 | Hela | MGC-803 |
|---|---|---|---|
| ICD | 568.92 | 581.23 | 388.27 |
| TICD | 40.02 | 31.34 | 49.575 |
| NICD | 51.12 | 44.10 | 62.08 |
| FICD | 17.16 | 26.51 | 16.64 |

TABLE 2-continued

Growth inhibition effect ($IC_{50}$: μM) of isocorydine derivatives
on 3 strains of cancer cells, HepG2, Hela, and MGC-803.

| Compound | HepG2 | Hela | MGC-803 |
|---|---|---|---|
| COM33(17) | 7.51 | 6.32 | 11.14 |
| Sorafenib | 15.00 | 12.01 | 19.92 |

It was indicated by those results that COM33, among derivatives of isocorydine, had the strongest growth inhibition effect on 3 strains of cancer cells and had a stronger anti-cancer activity than that of sorafenib. Meanwhile, it was demonstrated that tumor inhibition activities of isocorydine derivatives were gradually enhanced and druggabilities were gradually improved by the applicant of the patent by optimization of the chemical structure of the raw material isocorydine and anti-cancer activity screening.

Example 23

Research on Mechanism of Anti-Cancer Effect of FICD on Liver Cancer Cells

1. Growth inhibition effect of FICD on tumor cells and synergistic effect with sorafenib.

Figure 5:
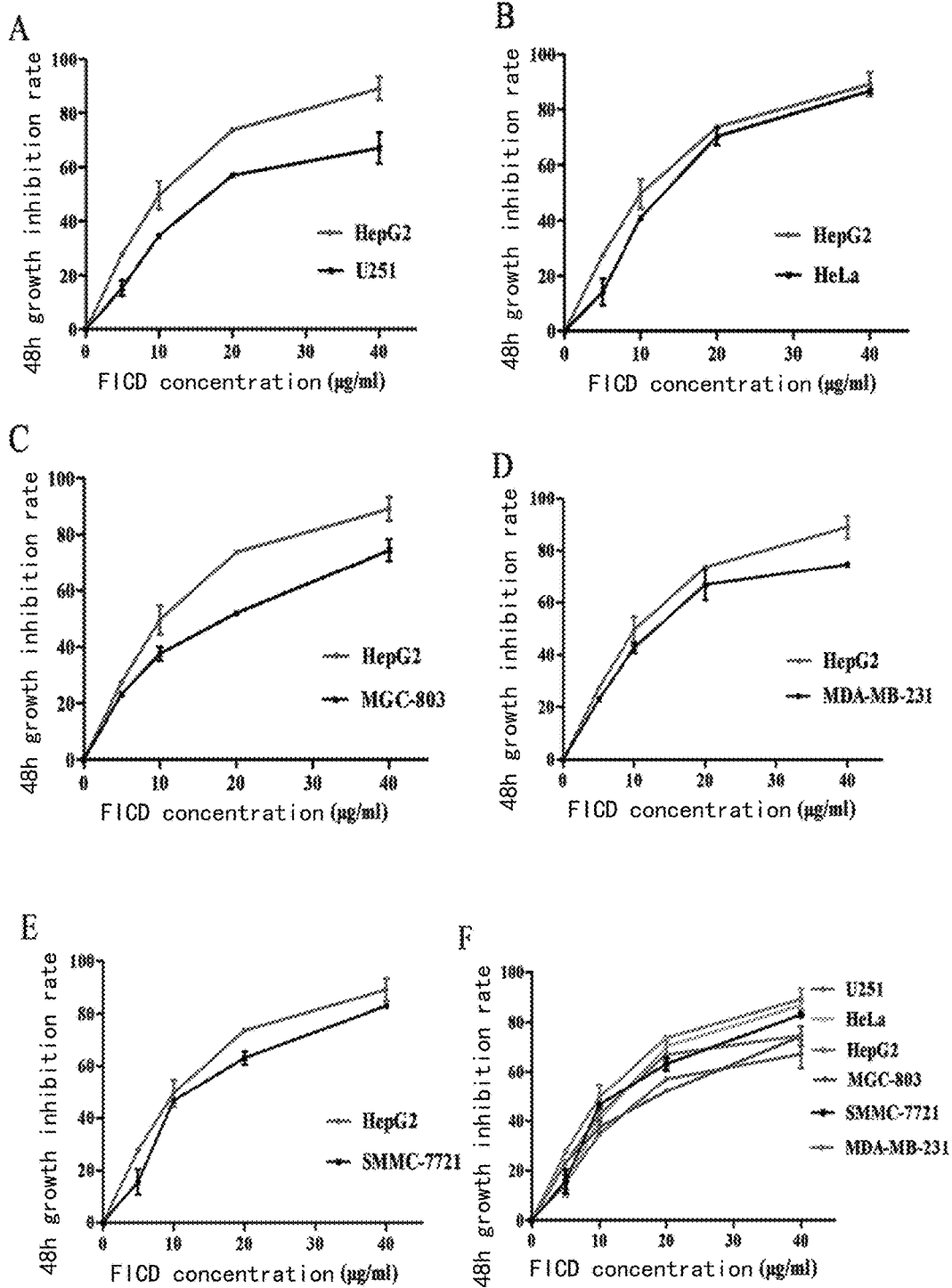
FIG. 5. Growth inhibition effect of FICD on 6 types of tumor cells, wherein the concentrations of FICD are 0, 5, 10, 20, and 40 µg/mL, respectively, and six strains of cells are U251, Hela, MGC-803, MAD-MB-231, SMMC-7721, and HepG2, respectively.

According to the MTT detection method in Example 21, tumor cell growth inhibition effect of the compound FICD on brain glioma U251, ovarian cancer Hela, gastric cancer cells MGC-803, liver cancer cells SMMC-7721, liver cancer cells HepG2, and breast cancer cells MAD-MB-231 were detected. Results can be seen in FIG. 5, and it was indicated that FICD in a concentration range of 10-40 μg/mL had certain growth inhibition activities for all of 6 types of tumor cells. Among these, the effect on human liver cancer HepG2 cells was the most significant.

As indicated by experimental researches, FICD had different effects on the proliferation of different cancer cell strains of humans, wherein FICD had the most significant inhibition on human liver cancer HepG2 cells, and FICD had dose and time dependent relationships for inhibition effect of different tumor cells in a concentration range of 10 to 40 μg/mL. After 48 h of action, $IC_{50}$ values of FICD for different cells were HepG2: 10.10±1.20 μg/mL, U251: 16.80±0.28 μg/mL, Hela: 18.60±0.29 μg/mL, MGC-803: 15.60±2.40 μg/mL, and MDA-MB-231: 14.20±0.66 μg/mL, respectively.

Figure 6:
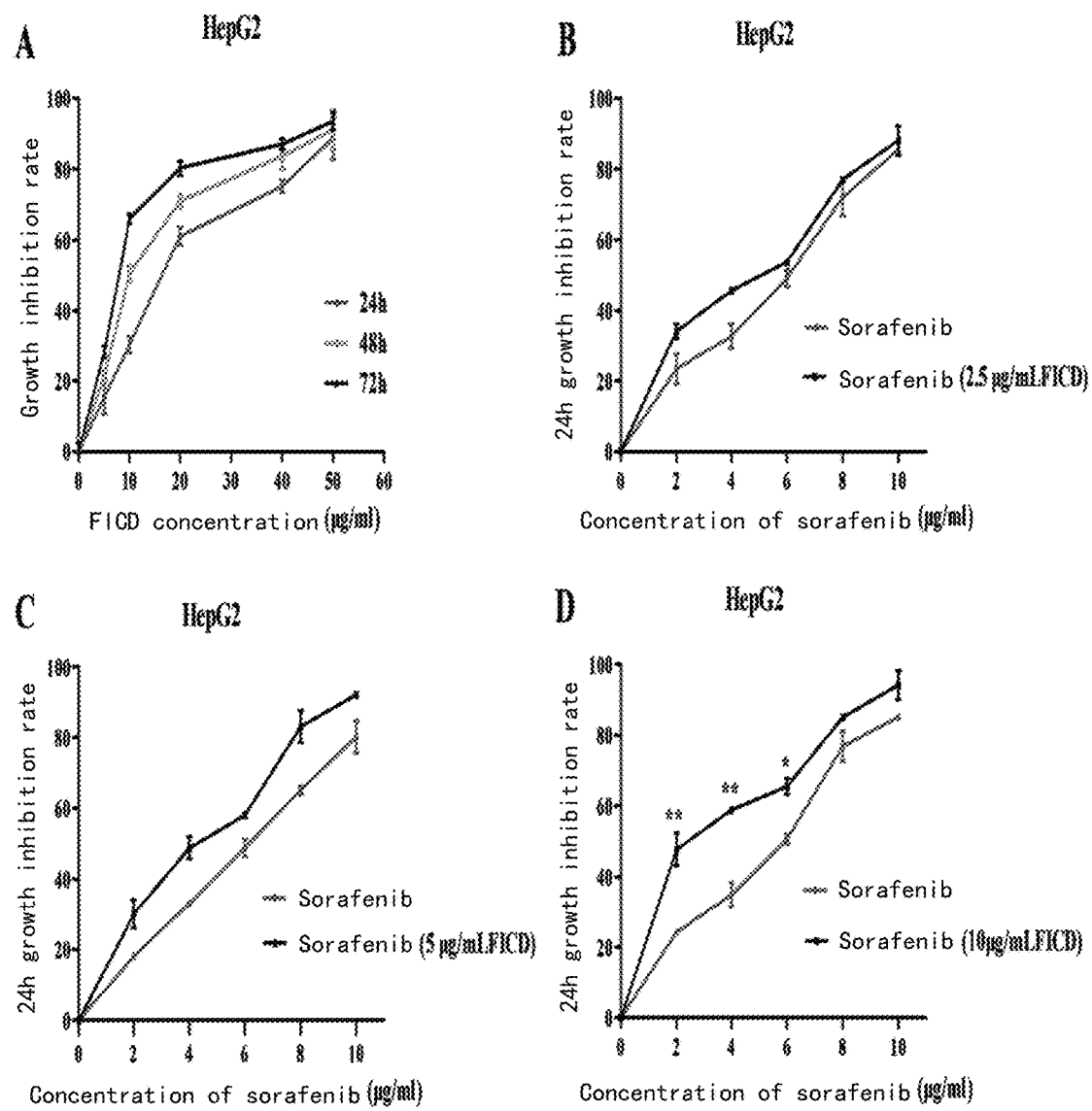
FIG. 6. Plots of growth inhibition effect of FICD on HepG2 and synergistic effect with sorafenib. (A, FICD has a dose and time dependent relationship with the growth of HepG2; and B, C, and D are growth inhibition effect of drug combination of FICD and sorafenib on HepG2).

It was indicated by researches that $IC_{50}$ of FICD for liver cancer cells was 10-20 μg/mL, the apoptosis of HepG2 may be induced after 24 h of action by FICD, and FICD had a time and dosage dependent relationship for the inhibition on tumor cell growth, wherein the inhibition rate was significantly increased as the time went and the inhibition rate was gradually increased as the concentration of administration was increased. Meanwhile, FICD had a synergistic effect with sorafenib (see FIG. 6 and Table 3).

TABLE 3

Synergistic effect of drug combination of FICD and sorafenib
on HepG2 growth inhibition ($IC_{50}$: μg/mL) and synergistic fold.

| Administration manner | $IC_{50}$ value (synergistic fold) | Administration manner | $IC_{50}$ value (synergistic fold) |
|---|---|---|---|
| Sorafenib | 12.4 ± 0.044 | S + 5 μg/mL | 8.97 (1.25) |
| S + 10 μg/mL FICD | 5.44 (2.04) | S + 2.5 μg/mL | 11.2 (0.91) |

Note:
S represents sorafenib.

2. Apoptosis induction effect of FICD on liver cancer cells.

2.1. Measurement of apoptosis induction effect of FICD on liver cancer cells by Annexin V and PI double-staining method:

Method: HepG2 cells in a logarithmic growth phase were taken, washed twice with PBS, digested with 0.25% trypsin, inoculated on a 6-well plate at $1.25 \times 10^5$/well after cell counting, and adherently cultured overnight. Different concentrations of FICD were added on the second day, culture was continued for 24 h, cells were collected and washed 3 times with precooled PBS, and adherent cells were digested with trypsin free of EDTA. The solutions were combined, centrifuged, and washed 3 times again with precooled PBS. 400 μL of solution containing 5 μL of V-FITC and 10 μL of PI was added, incubation was performed at room temperature under protection from light, and detection was performed by flowcytometry after 30 min.

Figure 7:
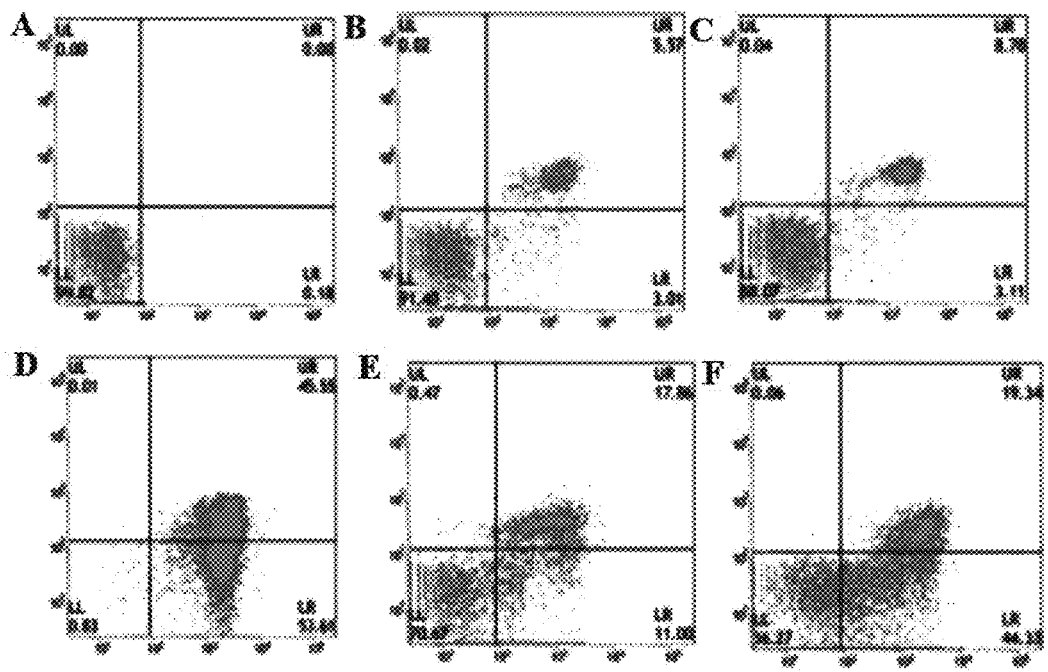
FIG. 7. Apoptosis induction effect of FICD and drug combination of FICD and sorafenib on HepG (A: a blank group using 0.1% DMSO, B: 2.5 µg/mL, C: 5 µg/mL, D: 20 µg/mL, E: sorafenib: 4 µg/mL, F: a drug combination group: 4 µg/mL sorafenib+5 µg/mL FICD).
Figure 8:
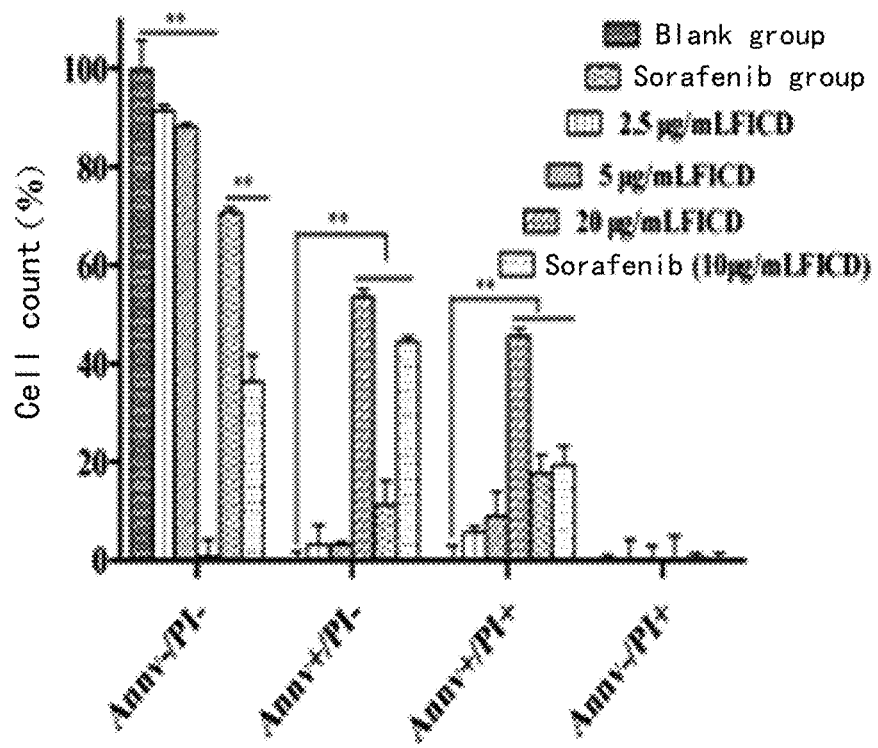
FIG. 8. Statistical results of apoptosis induction effect of FICD and drug combination of FICD and sorafenib on HepG (see FIG. 7).

Results can be seen in FIG. 7 and FIG. 8. As indicated by experimental researches, apoptosis rates of cells after a single-drug treatment of FICD and sorafenib were increased to 11.93% and 29.33%, respectively, compared to the control group, and the apoptosis rate of the drug combination group was further significantly increased and was up to 63.73%, and has a significant difference ($P<0.05$) compared to the single drug group.

Figure 9:
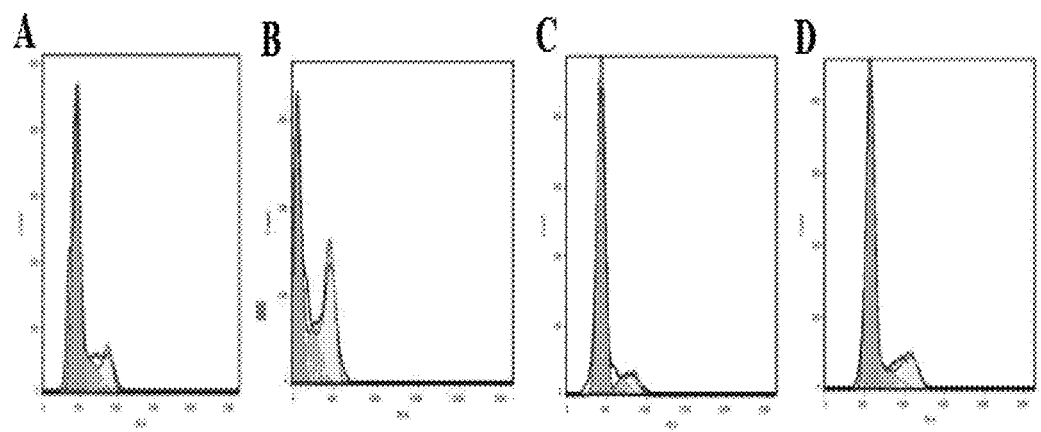
FIG. 9. Flow cytometry detections of cell cycle distributions resulted from the treatment of HepG2 with FICD and its combination with sorafenib (A, a blank control, B, a sorafenib group: 5 µg/mL; C, FICD: 10 µg/mL; D, drug combination group: 5 µg/mL FICD+10 µg/mL sorafenib).
Figure 10:
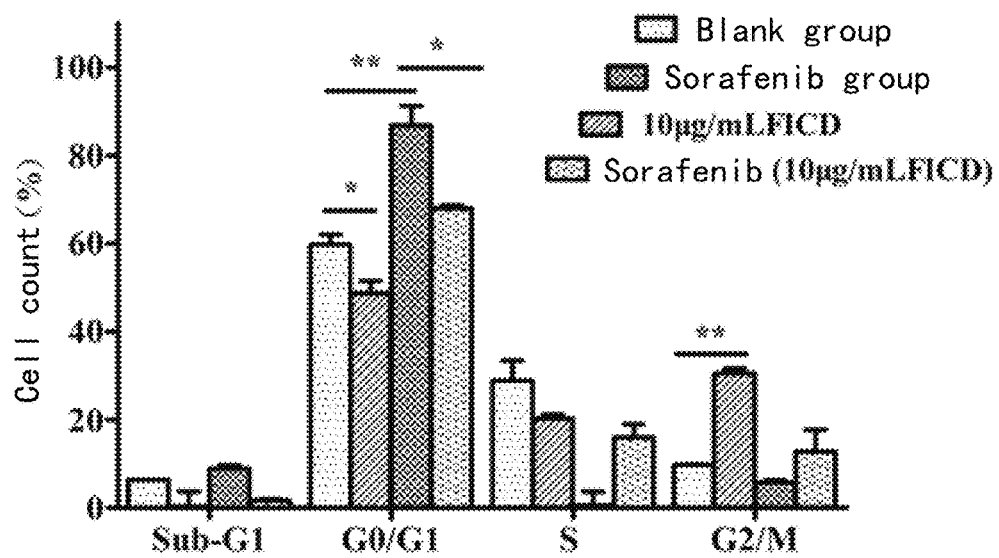
FIG. 10. Statistical results of flow cytometry detections of cell cycle distributions resulted from the treatment of HepG2 with FICD and its combination with sorafenib (see FIG. 9).

2.2. Detection of the effect of FICD on HepG2 cell cycle:

Method: HepG2 cells treated with FICD and sorafenib at different concentrations were collected and washed twice with PBS, adherent cells were digested by adding 0.25% trypsin free of EDTA, centrifuged at 1200 r/min in 10 min, the supernatant was discarded, 2 mL of precooled PBS was added for washing 3 times. 1 mL of 70% precooled (−20° C.) ethanol was added to the cell precipitate, homogenized by pipetting, and fixed at 4° C. overnight. On the second day, HepG2 cells was collected by centrifugation, 2 mL of precooled PBS was added for washing 3 times, 500 μL of PBS containing 50 μg/mL ethidium bromide (PI) and 100 μg/mL RNaseA was added, and incubation was performed at 4° C. under protection from light for 30 min. Detection was performed on a flow cytometer, and results can be seen in FIG. 9 and FIG. 10.

The cell cycle was measured by AnneixnV-FITC and PI double-staining, and effects of a blank control group, a sorafenib group, a 10 μg/mL FICD group, and a drug combination group on HepG2 cells were detected by experiments. With respect to the sorafenib group, cells significantly increased in the G0/G1 phase of the cell cycle and significantly decreased in the S phase, compared to the blank control group. With respect to the FICD administration group, cells significantly increased in the G2/M phase and decreased in the G0/G1 phase. With respect to the drug combination group, cells decreased in the G0/G1 phase and decreased in the S phase, and there was a significant difference and a statistical significance.

2.3. Detection of apoptosis induction effect of drug combination of FICD and sorafenib on HepG2 by laser confocal scanning microscope.

Method: Cell cultures obtained by treating HepG2 cells for 48 h with FICD, sorafenib, and a drug combination group of the both at different concentrations were collected, adherent cells were digested with 0.25% trypsin, the trypsin was discarded, and PBS was added. Two solutions (a former one and a later one) were mixed, centrifugation was performed at 1000 r/min for 5 min, the supernatant was discarded, and washing was performed for 3 times with PBS. The cell precipitate was resuspended in Binding Buffer, 10 μL of a FITC-Annen V staining liquid was added, homogenized by pipetting slightly, and reaction was performed under protection from light. PI was added for staining for 15 min, centrifugation was performed, the supernatant was discarded, and washing was performed for 3 times again with PBS. A glass slide was loaded by applying the cell precipitate thereto and mounted with non-fluorescent buffering glycerol, a laser confocal scanning microscope was immediately used for observation and taking photographs at wavelengths of 488 nm and 560 nm. Meanwhile, cells without AnneixnV-FITC and PI added were used as a negative control.

Figure 11:
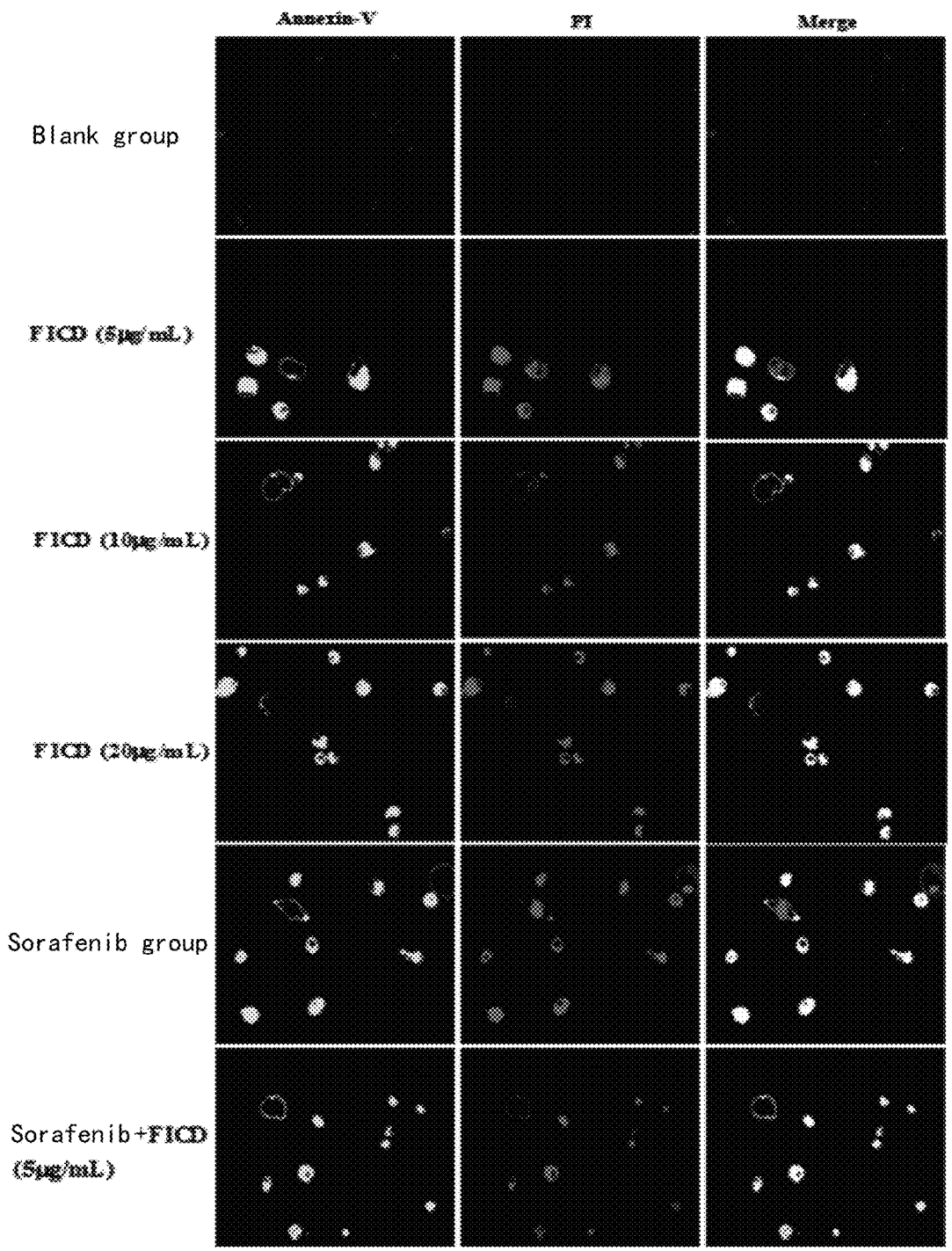
FIG. 11. Laser confocal detections of apoptosis induction effect of FICD on HepG2.

Results can be seen in FIG. 11. As indicated by experimental researches of Anneixn V-FITC and PI double-staining by laser confocal scanning microscope, in the blank group, the red and the green were not stained and only could be seen under an optical microscope. The cell morphology was normal and the cell membrane was complete. In the FICD treatment group, the sorafenib group, and the drug combination group, apoptoses occurred during various phases. The cell morphology changed, and the cell nucleus exhibited to be corrugated or partly wrinkled and subsequently became dense and hyperchromatic granular fluorescence. The chromatin was highly condensed and marginated. In the drug combination group, some cells were lysed to be fragments and apoptotic bodies were generated.

3. Detection of effect on protein expression by Western blotting after treatment of human liver cancer HepG2 cells with FICD.

Figure 12:
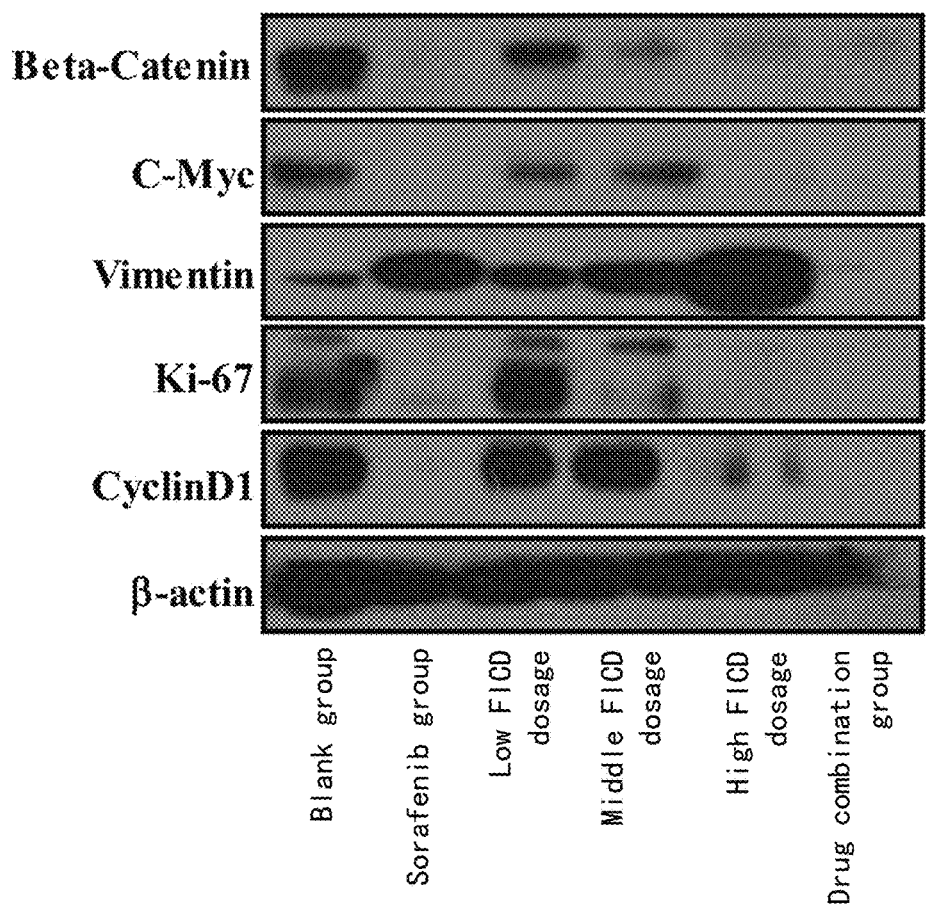
FIG. 12. Changes in protein expression levels in various groups of the treatment of hepatocellular carcinoma cells HepG2 with FICD (blank group: PBS; sorafenib group: 4 µg/mL; low FICD dosage group: 5 µg/mL; middle FICD dosage group: 10 µg/mL; high FICD dosage group: 20 µg/mL; drug combination group: 4 µg/mL sorafenib+10 µg/mL FICD).

Method: Gel electrophoresis of protein samples. Gel formulation: All components were added to a small beaker according to a formulation of a separation gel, uniformly mixed with slightly shaking to prevent the generation of bubbles, quickly applied to a seam of a glass plate with a 1 mL pipette, and then blocked with double distilled water to prevent oxidation. After 30 min, the separation gel solidified, the double distilled water thereof was poured off, waster was suctioned with a filter paper, a 5% concentration gel was formulated, TEMED was finally loaded onto the glass plate, and a 1.0 mm comb was inserted into the concentration gel and placed at room temperature for 30 min. The comb was slightly, vertically, and carefully pulled up, various groups of 20 μL protein samples were pipetted with a microsyringe, an equal volume of a loading buffer and an equal volume of a loading buffer containing 3 μL of Marker were separately added to a loading well, an electrophoresis instrument was switched on after electrodes were plugged, gels were run at 75V for 30 min, and the voltage was changed to 120V and gels were run for 2 h when bromophenol blue reaches the separation gel. Membrane transfer: A PVDF membrane having a suitable size was cut according to the size of the gel, placed in a methanol solution for 1 min, lifted, and placed and soaked together with a well cut filter paper in a previously precooled membrane transfer buffer. A sponge pad, three layers of filter paper, a gel, three layers of filter paper, and a sponge pad, in this order from top to bottom, were placed in a membrane transfer tank, and a precooled membrane transfer buffer was then added. Several ice bags were placed circumferentially to prevent an excessively hot external environment, and electrodes were plugged and membrane transfer was performed at a constant current of 200 A for 2.5 hours. Blocking and incubation of antibodies: A transferred membrane was cut into desired bands, which were placed in a blocking solution of 5% skim milk powder, placed on a shaker, and shaken at room temperature at a low speed for 1 h. A primary antibody was diluted with the blocking solution, a corresponding antibody was pipetted and added to a zip lock bag, the PVDF membrane was then placed in the antibody dilution, bubbles in the zip lock bag were evacuated, and the zip lock bag was sealed and placed in a refrigerator at 4° C. overnight. The membrane was withdrawn from the zip lock bag on the second day, and placed in a clean dish. A TBST solution was added and washed 3 times on a low-speed shaker, 10 min for each time. A secondary antibody was diluted with an appropriate amount of 5% skim milk powder, a corresponding antibody was pipetted and added to a zip lock bag, the PVDF membrane was then placed in the antibody dilution, bubbles in the zip lock bag were evacuated, and the zip lock bag was sealed and incubated for 2 h by placing at room temperature. The membrane was withdrawn and washed for 3 times with TBST, 10 min for each time. Development and fixation: An liquid A and a liquid B, which were used for chemiluminescence, were mixed at a volume ratio of 1:1, the PVDF membrane was placed on a plastic wrap on a dark box, a formulated luminescent agent was then slowly dropped on the PVDF membrane with approximately 100 μL on each membrane, reaction was performed for 2 min, the redundant chemiluminescent agent around the membrane was suctioned with a filter paper, and the plastic wrap covered the other side of the membrane. A cut film having a suitable size covered the membrane, the cap of the dark box was closed, and the time of exposure was adjusted according to the strength of light bands. After completion of exposure, the cap of the dark box was opened, and the film was withdrawn and placed in a developing solution. When the occurrence of bands was seen, the film was withdrawn and rinsed with distilled water, then placed in a fixing solution for 3 min, washed with distilled water to be clean, and dried in air. Results can be seen in FIG. 12.

Compared to the blank group, the expressions of oncoprotein C-Myc, protein Ki-67 related to cell growth, protein CylinD1 related to cell cycle, and β-Catenin protein of liver cancer cells were all significantly reduced in the sorafenib group, the high FICD dosage group, and the drug combination group, and there was a significant difference ($P<0.01$). It was demonstrated that FICD had the effects of inducing the apoptosis of liver cancer cells, blocking the growth of tumor cells, and significantly reducing cytoskeletal proteins, and could exert a tumor growth inhibition effect via the Wnt/β-Catenin signaling pathway. In the sorafenib group and the FICD group, Vimentin significantly increased, indicating that epithelial-mesonchymal transition (EMT) occurred in cells and stem cell properties of liver cancer cells were enhanced. However, Vimentin was not expressed in the drug combination group, demonstrating that EMT was effectively reversed in cells. Liver cancer stem cell properties were reduced and the drug resistance was reduced, which was disadvantageous to metastasis and invasion of liver cancer cells and significantly improved the anti-cancer activity of sorafenib and the reversion of drug resistance.

Example 24

In Vivo Tumor Growth Inhibition Effect of FICD on White Kunming Mice Bearing Ascites Hepatoma $H_{22}$ Induced Solid Tumor The aim of this experiment was to investigate in vivo tumor growth inhibition effect of FICD on white Kunming mice bearing ascites hepatoma H22 induced solid tumor, with respect to single FICD drug, drug combination of FICD and sorafenib, and different administration manners of FICD. The specific protocol of investigation was as follows:

Test Method:

1. Tumor strain and animal for experiments: $H_{22}$ liver cancer cell strain was provided by Teaching and Research Office, School of Basic Medical Sciences, Lanzhou University/Key Lab of Preclinical Study for New Drugs of Gansu Province, and was passage and preserved by periodically intraperitoneal inoculation. White Kunming mice (18.0-22.0 g) were provided by Lanzhou Veterinary Institute, Chinese Academy of Agriculture.

2. Establishment of tumor models and method of grouping: a third passage of mice which were well grown 7 d after intraperitoneal inoculation of $H_{22}$ tumor cells were sacrificed by cervical dislocation, and placed and soaked in 75% alcohol for 10 min. After 3 mL of sterile physiological saline was intraperitoneally injected, milky tumor cell ascites was withdrawn from the abdominal cavity, and formulated into a tumor cell suspension with sterile physiological saline, with a cell number of $1.5 \times 10^7$ $mL^{-1}$. 80 white Kunming mice were taken, and 0.2 mL of the tumor cell suspension was subcutaneously inoculated to the left axilla of each mouse. 24 h after the inoculation of tumor cells, the mice were divided into 8 groups according to body weights, 10 mice for each group. The groups were: a physiological saline model group; sorafenib positive control group, and the administration dosage was 50 mg/kg; there were 3 FICD treatment groups, and the administration dosages were 150 mg/kg (high dosage), 100 mg/kg (middle dosage), and 50 mg/kg (low dosage); and there were 3 drug combination groups, each of which contained sorafenib with a dosage of 50 mg/kg and FICD with one of 3 dosages (high, middle, and low), wherein high, middle, and low dosages were according to single FICD treatment groups. All of the administration manners were intraperitoneal administration.

3. Result of experiments: On the second day of modeling, continuous administration was performed for 10 d. Administration was stopped on the $11^{th}$ d, and mice were sacrificed by cervical dislocation on the next day. Complete tumor tissues were exfoliated, the wet weight was weighed, and the equation for calculating the tumor inhibition rate was as follows: Tumor inhibition rate (%)=(average tumor weight of control group−average tumor weight of administration group)/average tumor weight of control group×100%.

TABLE 4 in vivo tumor growth inhibition effect of FICD and drug combination of FICD and sorafenib on white Kunming mice bearing $H_{22}$ (n = 10)

| | Administration manner | | | | | | |
|---|---|---|---|---|---|---|---|
| | Sorafenib | High FICD dosage group | Middle FICD dosage group | Low FICD dosage group | High dosage group of drug combination | Middle dosage group of drug combination | Low dosage group of drug combination |
| Tumor inhibition rate (%) | 55.8 | 50.8 | 45.6 | 39.1 | 70.6 | 65.1 | 63.1 |

Note:
** represents a great significant difference, P < 0.01%; high dosage: 150 mg/Kg; middle dosage: 100 mg/Kg; low dosage: 50 mg/Kg. The dosages of sorafenib in the sorafenib group and the drug combination group were both 50 mg/Kg.

Figure 13:
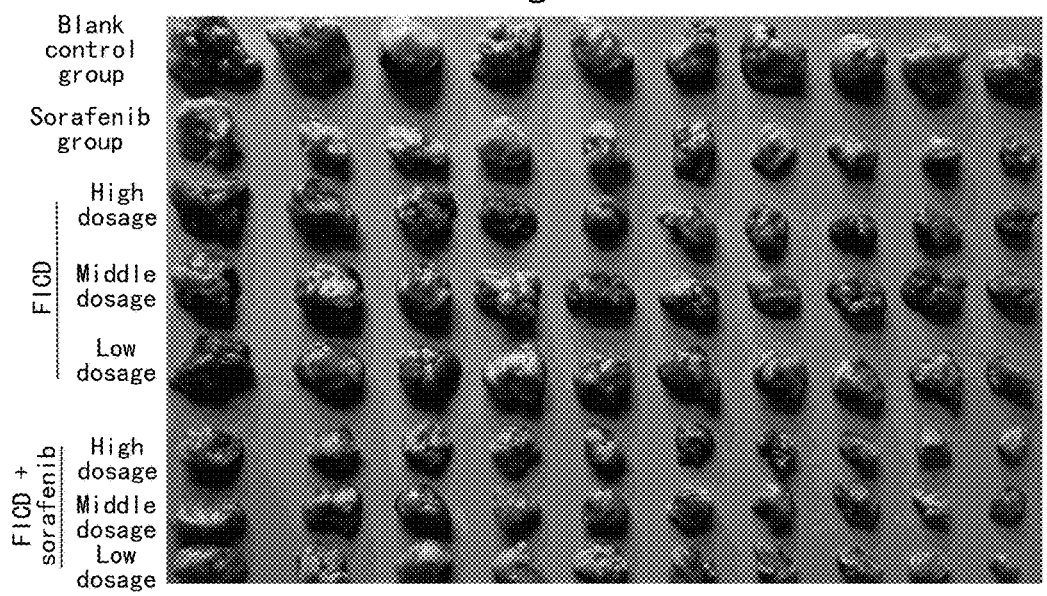
FIG. 13. In vivo tumor growth inhibition effect of FICD on mice bearing $H_{22}$ (wherein physiological saline is blank control group and sorafenib is positive control group, both of which employ intraperitoneal injection administration. High FICD dosage group: 150 mg/Kg, middle FICD dosage group: 100 mg/Kg, low FICD dosage group: 50 mg/Kg; drug combination group: the administration dosage of sorafenib is 50 mg/Kg).
Figure 14:
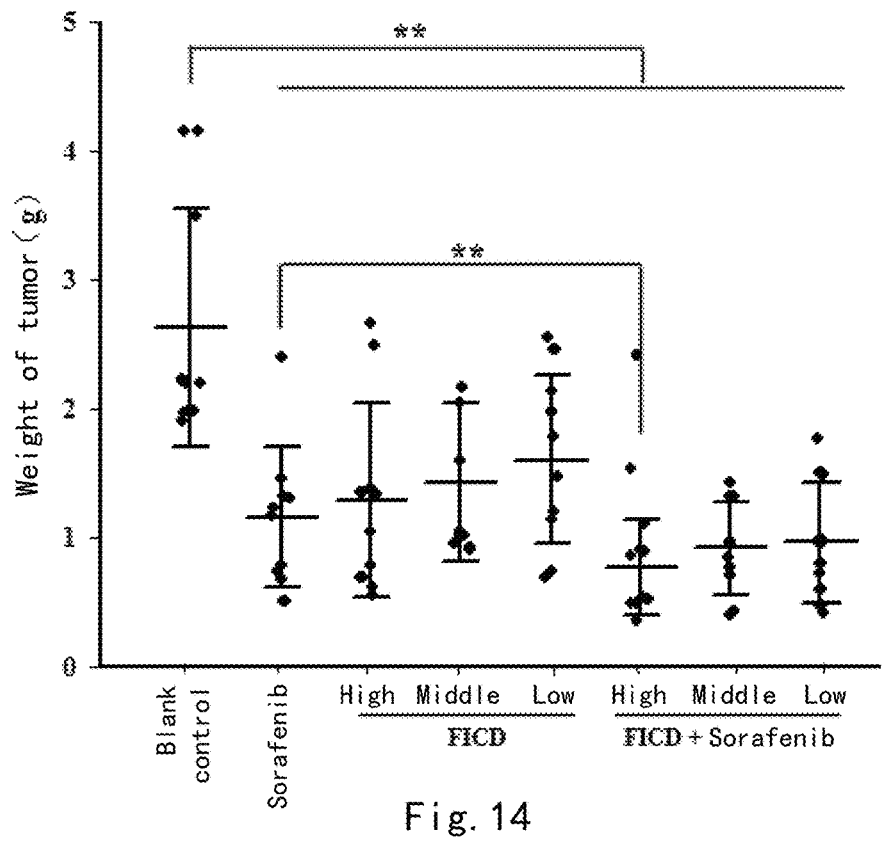
FIG. 14. Statistical results of data of in vivo tumor growth inhibition effect of FICD on mice bearing $H_{22}$ (see FIG. 13), wherein ** represents P<0.01 and there is a great significant difference.

Results can be seen in FIG. 13, FIG. 14, and Table 4. As indicated by researches, with respect to the in vivo effect of $H_{22}$, either the single FICD administration group or the drug combination group of FICD and sorafenib had a significant difference compared to the model control, and had a tumor inhibition rate greater than 40%. Furthermore, the drug combination group greatly improved the inhibition effect of FICD and had a remarkable synergistic effect. Drug combination of sorafenib with a dosage of 50 mg/Kg and FICD with a dosage of 150 mg/Kg could increase the tumor inhibition rate of sorafenib from 55.8% to 70.6%.

Example 25

Figure 15:
FIG. 15. In vivo tumor growth inhibition effect of FICD on mice bearing $H_{22}$ in different administration manners (wherein physiological saline is a blank control group, intraperitoneal injection administration groups wherein high dosage group: 150 mg/Kg, middle dosage group: 100 mg/Kg, and low dosage group: 50 mg/Kg; intragastric administration groups wherein high dosage group: 150 mg/Kg, middle dosage group: 100 mg/Kg, and low dosage group: 50 mg/Kg).
Figure 16:
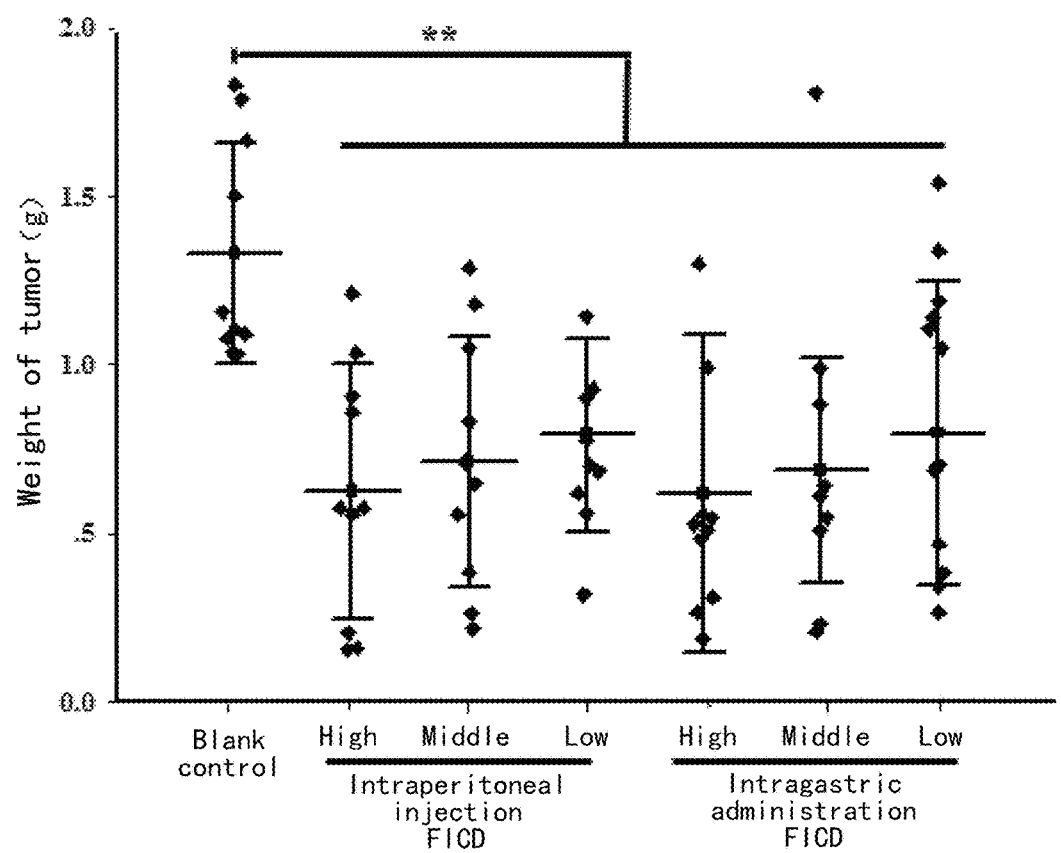
FIG. 16. Statistical results of data of in vivo tumor growth inhibition effect of FICD on mice bearing $H_{22}$ in different administration manners (see FIG. 15), wherein ** represents P<0.01 and there is a great significant difference.

In Vivo Tumor Growth Inhibition Effect of FICD on White Kunming Mice Bearing Ascites Hepatoma $H_{22}$ Induced Solid Tumor The aim of this experiment was to investigate in vivo tumor growth inhibition effect of FICD on white Kunming mice bearing ascites hepatoma $H_{22}$ induced solid tumor, discuss in vivo absorption of FICD in mice, and investigate the druggability and the selection of administration manners of FICD, among different administration manners (intragastric administration and intraperitoneal injection administration). The specific protocol of investigation was as follows:

Test method: For the test method, see Example 24. Results can be seen in FIG. 15, FIG. 16, and Table 5.

TABLE 5 in vivo tumor growth inhibition effect of FICD on white Kunming mice bearing H22 in different administration manners (n = 10)

| | Administration manner of FICD | | | | | |
|---|---|---|---|---|---|---|
| | Intraperitoneal injection | | | Intragastric administration | | |
| | High dosage | Middle dosage | Low dosage | High dosage | Middle dosage | Low dosage |
| Tumor inhibition rate (%) | 53.0 | 46.3 | 40.3 | 53.4 | 48.2 | 40.1 |

Note:
** represents a great significant difference, P < 0.01%; high dosage: 150 mg/Kg; middle dosage: 100 mg/Kg; low dosage: 50 mg/Kg.

As indicated by researches, with respect to FICD, either intragastrically administrated or administrated by intraperitoneal injection, the tumor inhibition rates for three administration dosages, 150 mg/Kg, 100 mg/Kg, and 50 mg/Kg, were all 40% or more, and were significantly different, compared to the model control. There was no statistical difference between administration manners, indicating that orally administrated FICD was well absorbed.

Example 26

3. Detection of Effect of COM33 on Protein Expression Activity of Liver Cancer HepG2 cells by Western Blotting Method: Differential expression of protein caused by the action of COM33 on HepG2 cells was characterized by using the Western blotting method as shown in item 3 of Example 23.

Figure 17:
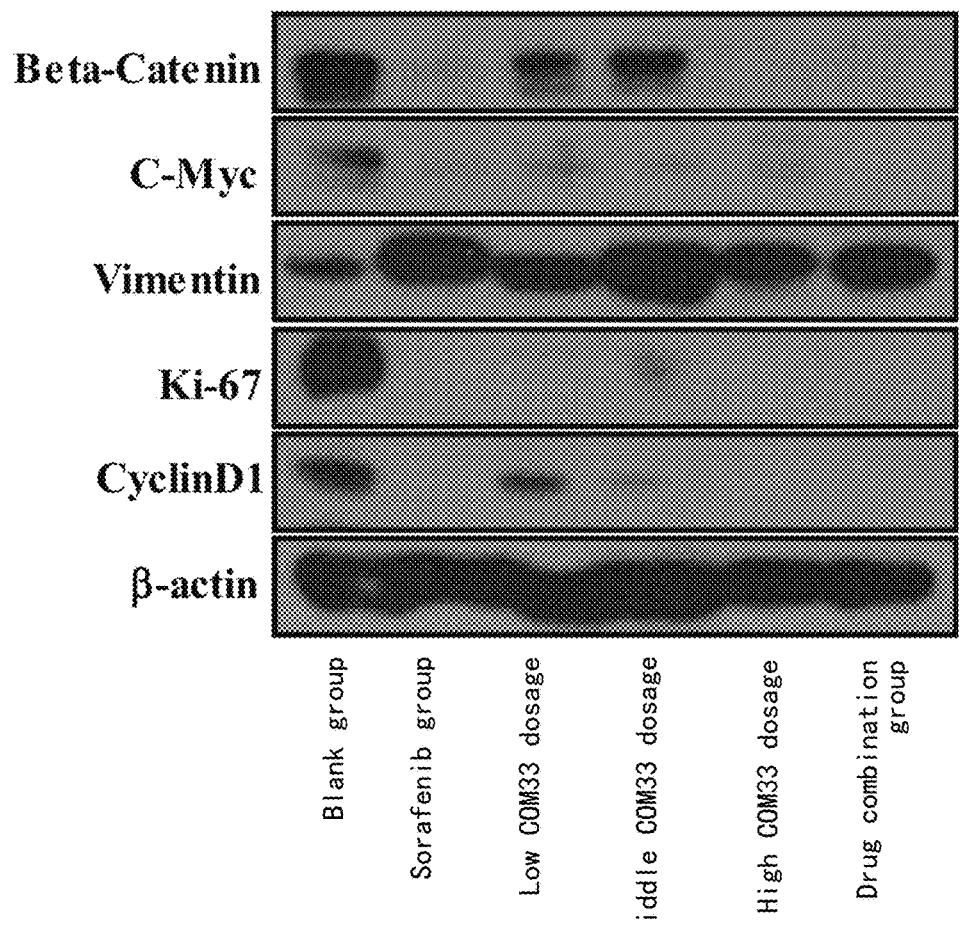
FIG. 17. Changes in protein expression levels in various groups of the treatment of hepatocellular carcinoma cells HepG2 with COM33 (physiological saline is blank group, sorafenib group: 4 µg/mL; low COM33 dosage group: 2.5 µg/mL; middle COM33 dosage group: 5.0 µg/mL; high COM33 dosage group: 10.0 µg/mL; drug combination group: 4 µg/mL sorafenib+5.0 µg/mL COM33).

Compared to the blank control group, the expressions of C-Myc, Ki-67, CylinD1, and β-Catenin protein of liver cancer cells were all significantly reduced in the sorafenib group, the high COM33 dosage group, and the drug combination group, (see FIG. 17) and there was a significant difference (P<0.01). It was demonstrated that COM33 had the effects of inducing the apoptosis of liver cancer cells, blocking the growth of tumor cells, and significantly reducing cytoskeletal proteins, and could exert a tumor growth inhibition effect via the Wnt/β-Catenin signaling pathway. Vimentin was expressed in all groups. Compared to the sorafenib group, the expression of Vimentin was significantly reduced in the drug combination group. It was indicated that COM33 had a synergistic effect with sorafenib and played a role in the reversion of drug resistance.

Example 27

In Vivo Tumor Growth Inhibition Effect of COM33 on White Kunming Mice Bearing Ascites Hepatoma $H_{22}$ Induced Solid Tumor Method: Modeling was performed by using the method of establishing $H_{22}$ white mice tumor-bearing model of Example 24. The in vivo tumor growth inhibition activity of COM33 on $H_{22}$ model mice was measured in an intraperitoneal injection administration manner.

TABLE 6 in vivo tumor growth inhibition effect of COM33 on white Kunming mice bearing $H_{22}$ (n = 10)

| | Groups of experiments | | | |
|---|---|---|---|---|
| | Sorafenib | High COM33 dosage group | Low COM33 dosage group | Drug combination group |
| Tumor inhibition rate (%) | 56.5 | 73.8 | 27.2 | 66.5 |

Note:
Administration mode: intraperitoneal injection, administration dosage: positive control sorafenib group (50 mg/Kg), high COM33 dosage group (100 g/Kg), low COM33 dosage group (50 mg/Kg), and drug combination group (sorafenib: 50 mg/Kg + COM33: 50 mg/Kg).

Figure 18:
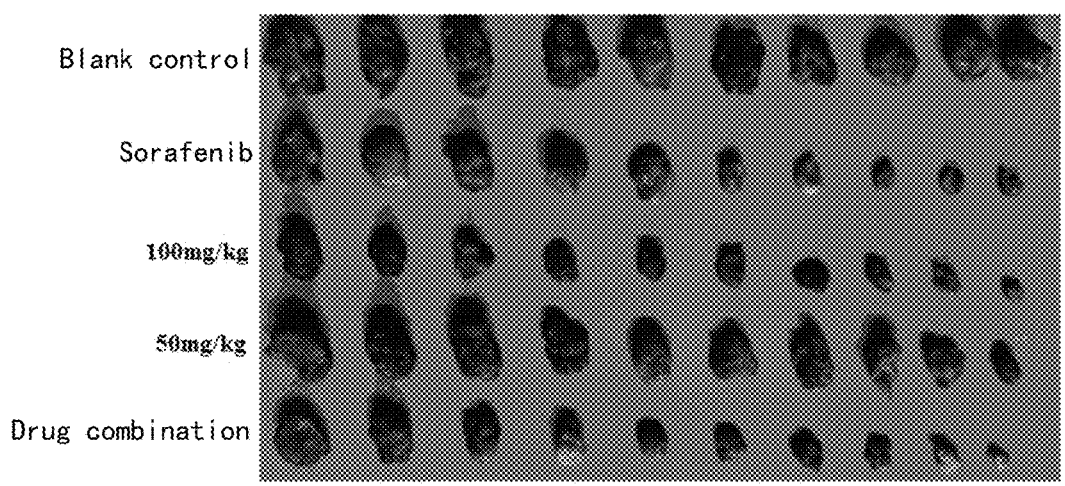
FIG. 18. In vivo tumor growth inhibition effect of COM33 on mice bearing $H_{22}$ (wherein PBS is blank control group; sorafenib is positive control group: with a dosage of 50 mg/Kg; high COM33 dosage group: 100 mg/Kg; low COM33 dosage group: 50 mg/Kg; drug combination group: 50 mg/Kg of sorafenib+50 mg/Kg of COM33, which all employ intraperitoneal injection administration).
Figure 19:
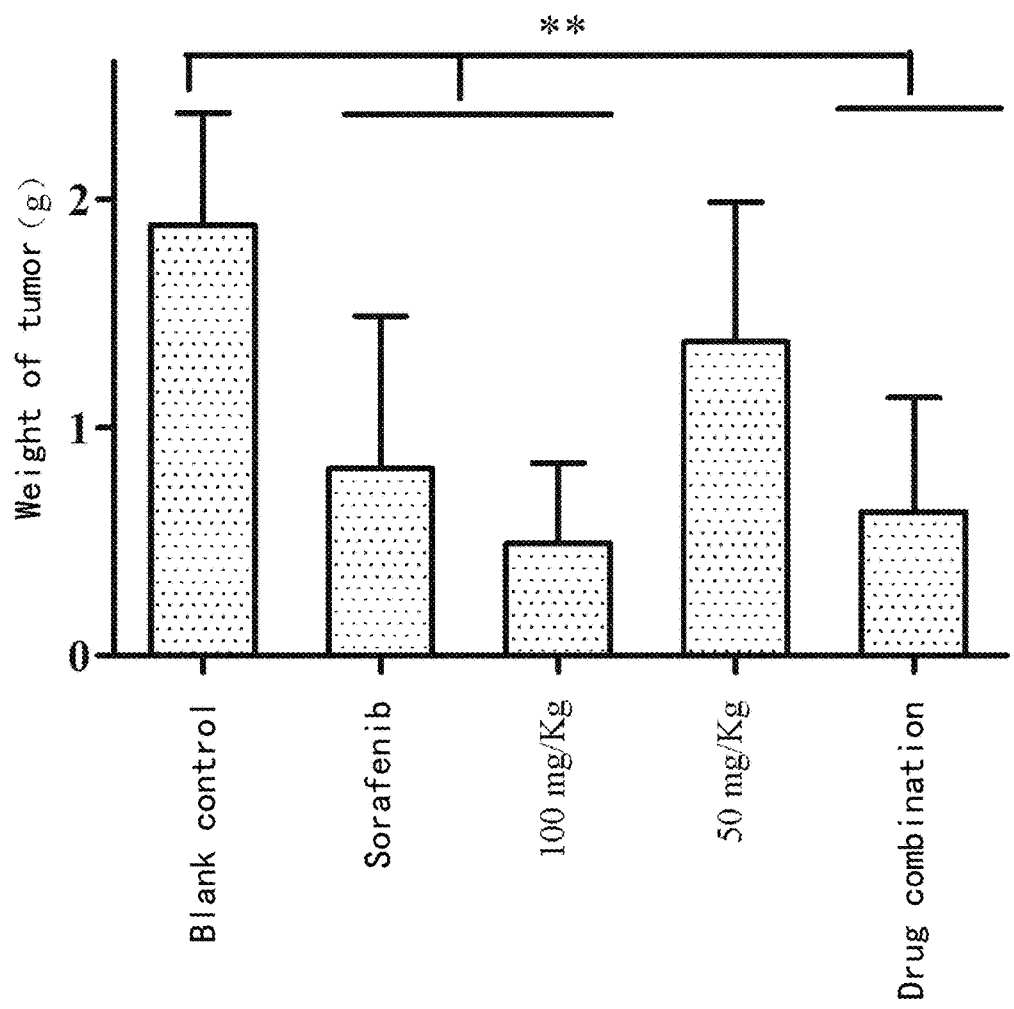
FIG. 19. Statistical results of data of in vivo tumor growth inhibition effect of COM33 on mice bearing $H_{22}$ (see FIG. 18), wherein ** represents P<0.01 and there is a great significant difference.

As indicated by researches, the tumor inhibition rate of sorafenib was 56.5%, and the tumor inhibition rate of sorafenib was relatively stable, which was verified by 3 sequential batches of experiments. It was demonstrated that the applicant could evaluate in vivo tumor growth inhibition effect of isocorydine derivatives by using this rapidly growing tumor model of $H_{22}$. The safety window of sorafenib was relatively limited. If the administration dosage of sorafenib was increased (50 mg/Kg or more), toxic and side effects of sorafenib would obviously occur, resulting in death of experimental animals (Results can be seen in FIG. 18, FIG. 19, and Table 6).

With respect to the in vivo tumor growth inhibition effect of $H_{22}$, either the single COM33 administration group or the drug combination group of COM33 and sorafenib were significantly different, compared to the model control, and had a tumor inhibition rate greater than 40%. Furthermore, drug combination could increase the tumor inhibition rate of sorafenib from 56.5% to 66.5%. It was indicated that COM33 had an additive or synergistic effect on the in vivo tumor inhibition effect of sorafenib. High-dosage COM33 could have a tumor growth inhibition rate of up to 73.8%, and the tumor inhibition rate was significantly higher than that of the positive control drug, sorafenib, and this compound has a relatively small influence on the weight of mice. It was indicated that COM33 had a relatively good in vivo tumor inhibition effect and relatively small toxic and side effects and the pharmaceutical characteristics were significantly superior to those of the clinical first-line therapeutic drug sorafenib, and had the prospect of new drug development.

What is claimed is:

1. A compound of formula I:

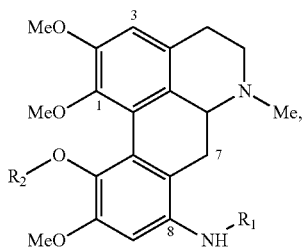

formula I wherein in formula I:
$R_1=$

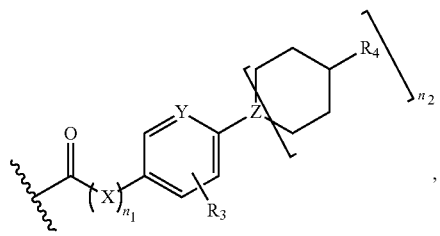

wherein
X=N, C, or C=C; $n_1$=0 or 1;
Y=C or N;
Z=H, Cl, F, or N; $n_2$=0 or 1;
$R_3$=H, Cl, Br, F, $CF_3$, $OCH_3$, $CH_3$, or

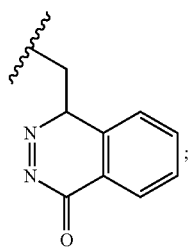 [SMILES: *CC1N=NC(=O)c2ccccc21]

$R_4$=$NH_2$, $CH_2NH_2$, $NHCO(CH_2)_{n3}CH_3$, or $CH_2NHCO(CH_2)_{n3}CH_3$, wherein n3=0, 1, or 2; and
$R_2$=H or $R_1$.

2. The compound according to claim 1, wherein in formula I, $R_2$=H, X=N, Y=C, $n_1$=1.

3. The compound according to claim 1, wherein in formula I, $R_2$=H, X=N, Y=C, $n_1$=1, Z=N, $n_2$=1.

4. A method for making the compound of formula I according to claim 1 comprising:
reacting NICD with an aryl isocyanate, a carboxylic acid, an acid chloride, or an aromatic amine in the presence of an organic solvent to obtain a reaction mixture comprising the compound of formula I; and
separating the compound of formula I from the reaction mixture.

5. The method of claim 4 comprising reacting NICD with the aryl isocyanate to form a ureido functional group, wherein an isocyanate is added to a solution of NICD in the organic solvent to perform a condensation reaction with stirring, the reaction solution is added to ice water after the reaction is complete, the solution is adjusted to be basic with an aqueous alkali solution, extraction is performed with dichloromethane, the solvent is recovered, and purification is conducted to obtain the compound of formula I.

6. The method of claim 5 wherein the isocyanate is selected from the group consisting of 4-chloro-3-trifluoromethylbenzene isocyanate, 2,4-dichlorobenzene isocyanate, 4-methylbenzene isocyanate, 4-methylthiobenzene isocyanate, 2-chlorobenzene isocyanate, 2-methylbenzene isocyanate, 4-trifluoromethylbenzene isocyanate, and 4-fluorobenzene isocyanate.

7. The method of claim 4 comprising: reacting NICD with the carboxylic acid or the acid chloride to form an amide functional group, wherein the carboxylic acid or the acid chloride is added to a solution of NICD in the organic solvent, a condensation catalyst is added to perform a condensation reaction with stirring, extraction is performed with dichloromethane after the reaction is complete, the solvent is recovered, and purification is conducted to obtain the compound of formula I.

8. The preparation method according to claim 7, wherein the carboxylic acid or acid chloride is selected from the group consisting of 4-chloro-3-trifluoromethylbenzoic acid, 4-chloro-3-trifluoromethylbenzoyl chloride, trans-cinnamic acid, trans-cinnamoyl chloride, (2E)-4-dimethylamino-2-butenoic acid, (2E)-4-dimethylamino-2-butenoyl chloride, nicotinic acid, nicotinoyl chloride, 5-[(3,4-dihydrogen-4-oxo-1-phthalazinyl)methyl]-2-fluorobenzoic acid, and 4-(4-methyl-1-piperazinylmethyl)-benzoic acid.

9. The method of claim 4 comprising reacting NICD with the aromatic amine, wherein the following steps are conducted:
step A: copolymerization reaction is performed between NICD and an aromatic amine in the organic solvent by solid phosgene or phosgene to form a ureido functional group: an arylamine, solid phosgene, and a condensation catalyst are added to a solution of NICD in the organic solvent to perform a condensation reaction with stirring, the solvent is recovered after the reaction is complete, and purification is conducted to obtain a resultant compound A;
step B: the resultant compound A obtained in the step A is dissolved in a second organic solvent, an aqueous alkali solution or protic acid is added to perform reaction with stirring, hydrolysis reaction of a protective group is performed, the second organic solvent is recovered after the reaction is complete, and purification is conducted to obtain a resultant compound B; and
step C: a carboxylic acid or an acid chloride is added to a third organic solvent solution of the resultant compound B obtained in the step B, reaction is performed with stirring to form aminoacylation protection, the third organic solvent is recovered after the reaction is complete, and purification is conducted to obtain the compound of formula I.

10. The preparation method according to claim 9 wherein the condensation catalyst in the step A is selected from the group consisting of triethylamine, benzotriazole-N,N,N',N'-tetramethyluronium hexafluorophosphate, and N,N-diisopropyl ethylamine.

11. A method of treating liver cancer comprising administering the compound of formula I according to claim 1 or a pharmaceutically acceptable salt thereof to a subject in need thereof.

* * * * *